United States Patent
Lei et al.

(10) Patent No.: US 9,687,424 B2
(45) Date of Patent: *Jun. 27, 2017

(54) POLYUREA CAPSULES PREPARED WITH ALIPHATIC ISOCYANATES AND AMINES

(71) Applicant: International Flavors & Fragrances Inc., New York, NY (US)

(72) Inventors: Yabin Lei, Holmdel, NJ (US); Li Xu, Newark, NJ (US); Carol Joyce, Toms River, NJ (US); Lewis Michael Popplewell, Morganville, NJ (US)

(73) Assignee: INTERNATIONAL FLAVORS & FRAGRANCES, New York, NY (US)

(*) Notice: Subject to any disclaimer, the term of this patent is extended or adjusted under 35 U.S.C. 154(b) by 28 days.

This patent is subject to a terminal disclaimer.

(21) Appl. No.: 13/969,038

(22) Filed: Aug. 16, 2013

(65) Prior Publication Data

US 2013/0337023 A1    Dec. 19, 2013

Related U.S. Application Data

(63) Continuation-in-part of application No. 13/163,320, filed on Jun. 17, 2011, which is a continuation-in-part of application No. 12/883,337, filed on Sep. 16, 2010, now abandoned, which is a continuation-in-part of application No. 12/562,578, filed on Sep. 18, 2009, now Pat. No. 8,299,011.

(51) Int. Cl.
| | | |
|---|---|---|
| *A61K 8/11* | (2006.01) | |
| *A61Q 5/02* | (2006.01) | |
| *A61Q 5/12* | (2006.01) | |
| *A61K 8/73* | (2006.01) | |
| *A61K 8/84* | (2006.01) | |
| *A61Q 19/10* | (2006.01) | |
| *B01J 13/14* | (2006.01) | |
| *B01J 13/16* | (2006.01) | |
| *C11D 3/50* | (2006.01) | |
| *C11D 17/00* | (2006.01) | |
| *B01J 13/20* | (2006.01) | |
| *A61Q 5/00* | (2006.01) | |

(52) U.S. Cl.
CPC ............ *A61K 8/11* (2013.01); *A61K 8/731* (2013.01); *A61K 8/84* (2013.01); *A61Q 5/00* (2013.01); *A61Q 5/02* (2013.01); *A61Q 5/12* (2013.01); *A61Q 19/10* (2013.01); *B01J 13/14* (2013.01); *B01J 13/16* (2013.01); *B01J 13/206* (2013.01); *C11D 3/505* (2013.01); *C11D 17/0039* (2013.01); *A61K 2800/412* (2013.01); *A61K 2800/624* (2013.01)

(58) Field of Classification Search
CPC . A61K 8/11; A61K 8/731; A61K 8/84; A61K 2800/412; A61K 2800/624; A61Q 5/12; A61Q 5/02; A61Q 19/10; A61Q 5/00; B01J 13/14; B01J 13/16; B01J 13/206; C11D 3/505; C11D 17/0039
See application file for complete search history.

(56) References Cited

U.S. PATENT DOCUMENTS

| | | | |
|---|---|---|---|
| 3,743,601 A | 7/1973 | Schnoring et al. | |
| 3,963,680 A * | 6/1976 | O'Keefe et al. | ............... 528/53 |
| 4,280,833 A | 7/1981 | Beestman et al. | ............. 504/300 |
| 4,563,212 A | 1/1986 | Becher et al. | |
| 4,640,709 A | 2/1987 | Beestman | ..................... 504/300 |
| 4,785,048 A | 11/1988 | Chao et al. | |
| 4,798,862 A | 1/1989 | Gillis et al. | |
| 5,164,126 A * | 11/1992 | Kalishek et al. | ........ 428/402.21 |
| 5,304,448 A | 4/1994 | Keoshkerian et al. | .... 430/110.2 |
| 5,324,584 A * | 6/1994 | Juang et al. | ..................... 264/4.7 |
| 5,635,211 A | 6/1997 | Nehen et al. | .................. 424/489 |
| 5,705,174 A | 1/1998 | Benoff et al. | |
| 5,866,153 A | 2/1999 | Hasslin et al. | |
| 5,925,595 A | 7/1999 | Seitz et al. | ..................... 504/359 |
| 6,133,197 A | 10/2000 | Chen et al. | .................. 504/359 |
| 6,340,653 B1 * | 1/2002 | Scher et al. | .................. 504/112 |
| 6,586,107 B2 | 7/2003 | Klug et al. | ..................... 503/215 |
| 6,797,670 B2 * | 9/2004 | Kleban et al. | ................ 503/215 |
| 7,125,835 B2 | 10/2006 | Bennett et al. | |
| 7,632,789 B2 | 12/2009 | Brain et al. | |
| 8,026,206 B2 | 9/2011 | Sajic et al. | |
| 8,299,011 B2 | 10/2012 | Lei et al. | ..................... 510/438 |
| 2002/0079599 A1 | 6/2002 | Kleban et al. | .................. 264/4.1 |
| 2004/0121155 A1 | 6/2004 | Matsunami et al. | |
| 2004/0156742 A1 | 8/2004 | Milan et al. | |
| 2005/0153135 A1 | 7/2005 | Popplewell et al. | |
| 2005/0153839 A1 | 7/2005 | Tamura et al. | |
| 2005/0161843 A1 | 7/2005 | Wang et al. | |
| 2005/0271735 A1 | 12/2005 | Stover et al. | .................. 424/490 |
| 2007/0042182 A1 * | 2/2007 | Markus et al. | ............. 428/402.2 |
| 2007/0138672 A1 | 6/2007 | Lee et al. | |
| 2007/0202063 A1 | 8/2007 | Dihora et al. | |
| 2008/0103265 A1 | 5/2008 | Schocker et al. | |
| 2008/0131695 A1 | 6/2008 | Aouad et al. | ................. 428/338 |
| 2008/0187596 A1 * | 8/2008 | Dihora | ..................... A61K 8/11 424/490 |
| 2008/0200363 A1 | 8/2008 | Smets et al. | ................... 510/475 |
| 2008/0206291 A1 | 8/2008 | Ouali et al. | ..................... 424/401 |
| 2009/0053161 A1 | 2/2009 | Nguyen et al. | ............. 424/70.17 |

(Continued)

FOREIGN PATENT DOCUMENTS

| | | |
|---|---|---|
| EP | 1693104 A1 | 8/2006 |
| JP | 5068970 A | 6/1975 |

(Continued)

OTHER PUBLICATIONS

Office Communication dated Oct. 18, 2011 from U.S. Appl. No. 12/562,578, filed Sep. 18, 2009.

(Continued)

*Primary Examiner* — Anoop Singh
*Assistant Examiner* — Doan Phan
(74) *Attorney, Agent, or Firm* — Martin Zhang; XuFan Tseng; Elizabeth M. Stover

(57) ABSTRACT

Polyurea capsules that encapsulate active materials in polymeric walls resulting from the polymerization of an aliphatic polyisocyanate and a cross-linking agent such as a diamine, amphoteric amine or guanidine amine/salt are provided as are consumer products containing said polyurea capsules and for methods for producing such capsules.

11 Claims, 3 Drawing Sheets

(56) References Cited

U.S. PATENT DOCUMENTS

| | | |
|---|---|---|
| 2010/0009893 A1 | 1/2010 | Cavin et al. |
| 2010/0086575 A1 | 4/2010 | Dihora et al. |
| 2010/0119679 A1 | 5/2010 | Dihora et al. ............... 426/534 |
| 2011/0077188 A1 | 3/2011 | Ouali et al. ..................... 512/2 |
| 2011/0077375 A1 | 3/2011 | Kulke |
| 2011/0230390 A1 | 9/2011 | Ouali et al. |
| 2012/0016139 A1 | 1/2012 | Screen et al. |
| 2012/0148644 A1 | 6/2012 | Popplewell et al. |
| 2013/0109569 A1 | 5/2013 | Dave et al. |
| 2013/0330292 A1 | 12/2013 | Lei et al. |
| 2013/0337023 A1 | 12/2013 | Lei et al. |
| 2014/0017287 A1 | 1/2014 | Lei et al. |

FOREIGN PATENT DOCUMENTS

| | | |
|---|---|---|
| WO | WO 2004/098767 | 11/2004 |
| WO | WO 2006/006003 | 1/2006 |
| WO | 2007137441 A1 | 12/2007 |
| WO | WO 2008031241 A1 * | 3/2008 |
| WO | 2009091726 A1 | 7/2009 |
| WO | 2009103615 A1 | 8/2009 |
| WO | WO 2011/154893 | 12/2011 |
| WO | WO 2012/107323 | 8/2012 |
| WO | WO 2013/000587 | 1/2013 |
| WO | 2013059167 A2 | 4/2013 |
| WO | 2013092958 A1 | 6/2013 |

OTHER PUBLICATIONS

Office Communication dated Aug. 21, 2012 from U.S. Appl. No. 13/163,320, filed Jun. 17, 2011.

Office Communication dated Nov. 21, 2012 from U.S. Appl. No. 13/163,320, filed Jun. 17, 2011.

Dow Plastics—"PAPI 135". Retrieved on Jan. 3, 2017. Retrieved from the internet <URL: http://msdssearch.dow.com/PublishedliteratureDOWCOM/dh_003f/0901b8038003f163.pdf>.

Chinese First Office Action issued Jan. 30, 2014 for Application No. CN 201010548980.0(with English Translation included).

* cited by examiner

POLYUREA CAPSULES PREPARED WITH ALIPHATIC ISOCYANATES AND AMINES

INTRODUCTION

This application is a continuation-in-part of U.S. patent application Ser. No. 13/163,320, filed Jun. 17, 2011, which is a continuation-in-part of U.S. patent application Ser. No. 12/883,337, filed on Sep. 16, 2010, now abandoned, which is a continuation-in-part of U.S. patent application Ser. No. 12/562,578, filed on Sep. 18, 2009, now U.S. Pat. No. 8,299,011, the contents of which are incorporated herein by reference in their entirety.

BACKGROUND

Microencapsulation is used in a variety of different applications where a compound needs to be delivered or applied to a target area, protected from its environment, or released in a time-delayed way or only after a treatment has been applied that triggers release. Various techniques for preparing microcapsules are known in the art and are used, depending on the contents to be encapsulated, the environment in which the microcapsules should retain their integrity and the desired release mechanism.

Interfacial polycondensation is a known technique for preparing microcapsules and versatile microcapsule wall materials are used including polyureas and polyurethanes (WO 2011/154893, WO 2012/107323, US 2011/0077188, U.S. Pat. No. 5,635,211, U.S. Pat. No. 6,586,107, and U.S. Pat. No. 6,797,670). Such wall materials are produced by having a first phase which is water-immiscible and includes a polyfunctional isocyanate, i.e., a diisocyanate and/or a polyisocyanate, and a second aqueous phase that may include a polyfunctional alcohol or amine, i.e., a diol and/or polyol, for obtaining a polyurethane capsule wall or a diamine and/or polyamine having —$NH_2$ and/or —NH groups.

If the active material to be encapsulated is hydrophobic, it will be included in the water-immiscible phase, thereafter the two phases are mixed by high shear mixing to form an oil-in-water emulsion. In this emulsion, the polycondensation reaction will take place. Thus, the small droplets of the water-immiscible phase will be surrounded by the microcapsule wall formed by polycondensation of the isocyanate and the polyalcohol or polyamine as starting materials. Conversely, if the material to be encapsulated is hydrophilic, it will be included in the aqueous phase and the mixture of the two phases converted into a water-in-oil emulsion. The polycondensation reaction will then form microcapsule walls surrounding the droplets of water-miscible phase. Suitable emulsifiers are often utilized to aid in the preparation and stabilization of the emulsion.

Suitable raw materials and processes for preparing microcapsules by polycondensation are described in U.S. Pat. No. 4,640,709 and the literature described therein. As is exemplified therein, and also in U.S. Pat. No. 6,133,197, polyurea and polyurethane microcapsules are often used for rugged applications, such as for encapsulation of agrochemicals, e.g., herbicides and pesticides, where slow time-release is desired to set the agents free. For such applications, the microcapsules also require a relatively high mechanical strength. For the polycondensation reaction, suitable diisocyanate and symmetrical triisocyanate starting materials are disclosed in the prior art.

U.S. Pat. No. 5,304,448 describes an encapsulated toner composition using reaction of amino acids and polyisocyanates.

Polyurea or polyurethane microcapsules have thus far not be applied for the release of benefit agents intended for laundry, washing, cleaning, surface care and personal and skin care. For such applications quicker and easier release and/or less mechanical strength are often desirable. Also, it would be desirable to more precisely influence the capsule wall permeability and other capsule wall properties to achieve the desired release profile and consumer benefits.

SUMMARY OF THE INVENTION

This invention is a method for preparing a polyurea capsule composition by preparing an oil phase comprising an active material and an polyisocyanate (e.g., an aliphatic or aromatic polyisocyanate); preparing a surfactant solution; emulsifying the oil phase into the surfactant solution to form a fragrance emulsion; adding a cross-linking agent to the fragrance emulsion to form a capsule slurry; and curing the capsule slurry. In one embodiment, the active material is a fragrance oil. In certain embodiments, the aliphatic polyisocyanate is oligomeric hexamethylene diisocyanate. In other embodiments, the surfactant is polyvinyl alcohol, polystyrene sulfonate, carboxymethyl cellulose, sodium salt of naphthalene sulfonate condensate, or a mixture thereof. In still other embodiments, the cross-linking agent is an amine such as a diamine (e.g., ethylenediamine, 1,3-diaminopropane, 1,4-diaminobutane, hexanethylene diamine, hexamethylene diamine or pentaethylenehexamine), a guanidine amine or salt (e.g., 1,3-diaminoguanidine monohydrochloride, 1,1-dimethylbiguanide hydrochloride, guanidine carbonate or guanidine hydrochloride), or an amphoteric amine (e.g., gelatin, L-lysine, D-lysine, L-arginine, D-arginine, L-lysine monohydrochloride, D-lysine monohydrochloride, L-arginine monohydrochloride, D-arginine monohydrochloride, L-ornithine monohydrochloride, D-ornithine monohydrochloride or a mixture thereof). In certain embodiments, the fragrance emulsion further includes sodium carbonate. In yet other embodiments, the step of adding the cross-linking agent to the fragrance emulsion is at a temperature of 35° C. or 22° C. In particular embodiments, the capsule slurry is cured at a temperature greater than about 55° C., 65° C., 75° C., 85° C. or 95° C. In a further embodiment, the method further includes the steps of adding a salt to the cured capsule slurry and washing the capsule slurry with water. In yet another embodiment, the step of curing the capsule slurry is carried out in the presence of a catalyst.

A polyurea capsule composition, optionally containing a deposition aide, and consumer product containing said polyurea capsule composition are also provided, wherein the consumer product can be in the form of a shampoo, rinse, hair conditioner, cream, body wash, body soap, body liquid detergent, hair refresher, hair lotion, personal cleaner, personal sanitizer or fabric refresher.

DETAILED DESCRIPTION OF THE INVENTION

Figure 1A:
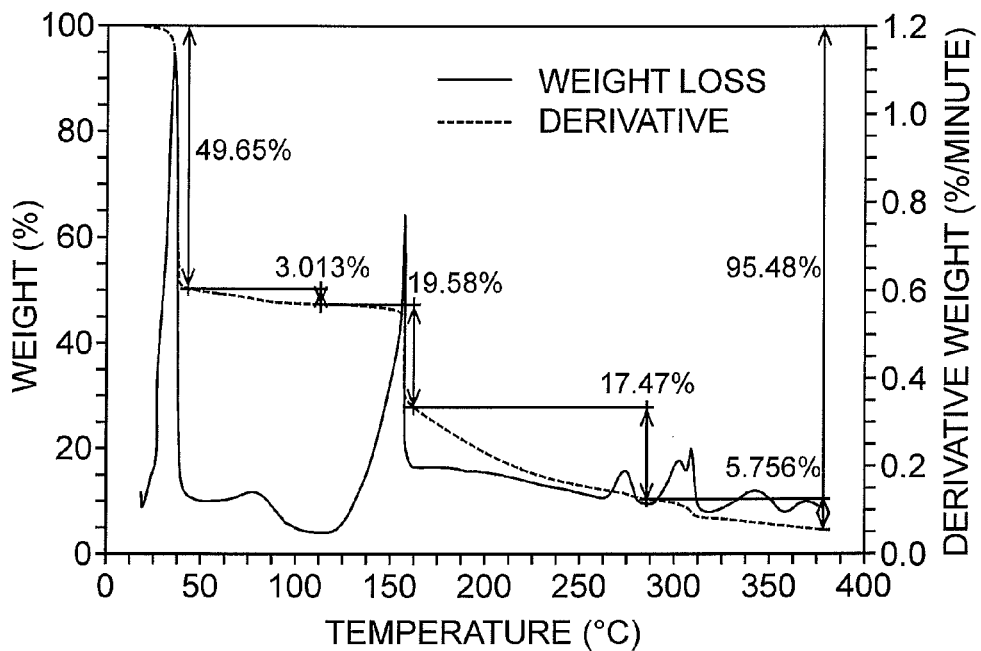
FIGS. 1A-1D show thermogravimetric analyses of samples prepared with polyvinyl alcohol (PVA) and carboxymethyl cellulose (CMC)(FIGS. 1A and 1D); PVA and Polyquaternium-44 (FIG. 1B); or PVA alone (FIG. 1C). These results demonstrate the thermal stability of the samples prepared with a capsule formation aid. Polyurea capsules of FIGS. 1A-1C were prepared with the aliphatic polyisocyanate DESMODUR N100 and guanidine carbonate, whereas the polyurea capsules of FIG. 1D were prepared with the aliphatic polyisocyanate DESMODUR 3600 and guanidine carbonate.

It has been found that polyurea microcapsules are very suitable for carrying various kinds of hydrophobic or hydrophilic benefit agents that are suitable for use in products intended for application to animate and inanimate surfaces. Moreover, the inclusion of a capsule formation aid in the polymerization reaction provides a microcapsule with excellent storage stability and retention of an encapsulated fragrance.

Therefore, this invention is a microcapsule composition and related process, wherein said microcapsule is composed of an encapsulating polymer and an active material encapsulated by the encapsulating polymer, wherein the encapsulating polymer is the reaction product of polymerization between at least one polyisocyanate, a cross-linking agent and a capsule formation aid.

Polyisocyanate.

In one embodiment of the invention, the encapsulating wall material of the microcapsule contains one or more aliphatic polyisocyanates. Exemplary aliphatic polyisocyanates of use as precursors in this invention include are commercially available and include, but are not limited to, BAYHYDUR N304 and BAYHYDUR N305, which are aliphatic water-dispersible polyisocyanates based on hexamethylene diisocyanate; DESMODUR N3600, DESMODUR N3700, and DESMODUR N3900, which are low viscosity, polyfunctional aliphatic polyisocyanates based on hexamethylene diisocyanate; and DESMODUR 3600 and DESMODUR N100 which are aliphatic polyisocyanates based on hexamethylene diisocyanate, each of which is available from Bayer Corporation, Pittsburgh, Pa.).

In another embodiment, the encapsulating wall material of the microcapsule contains one or more aromatic polyisocyanates. Desirably the aromatic polyisocyanate includes a phenyl, a toluyl, a xylyl, a naphthyl or a diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

In general, the average molecular weight of the polyisocyanate in the formulation of this invention varies from 2500 to 250 and preferable from 1500 to 275, most preferable from 500 to 275. In general, the range of the polyisocyanate concentration in the composition of this invention varies from 10% to 0.1%, preferably from about 7.5% to about 1%, preferably from about 5% to 0.25%, and most preferably from about 3.5% to about 1.5% of the total capsule suspension.

Cross Linking Agent.

In another embodiment of the invention, the encapsulating wall material of the polyurea capsule contains a cross-linking agent or material, including but not limited to an amine. Examples of amines of particular use include guanidine amines/salts, amphoteric amines, diamines, polyamines or a combination thereof.

Water soluble diamines are one class of amines of use in this invention as the amine is usually present in the aqueous phase. One class of such amine is of the type:

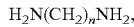

where n is ≥1. When n is 1, the amine is a diamine, ethylene diamine. When n is 2, the amine is diamine propane and so on. Exemplary amines of this type include, but are not limited to, ethylenediamine, 1,3-diaminopropane, 1,4-diaminobutane, hexanethylene diamine, hexamethylene diamine, and pentaethylenehexamine. In particular embodiments of this invention, the preferred n is 6, where the amine is a hexamethylene diamine.

Amines that have a functionality greater than 2, but less than 3 and which may provide a degree of cross linking in the shell wall are the polyalykylene polyamines of the type

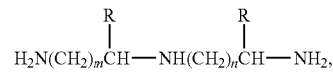

where R equals hydrogen or —CH$_3$, m is 1-5 and n is 1-5, e.g., diethylene triamine, triethylene tetraamine and the like. Exemplary amines of this type include, but are not limited to diethylenetriamine, bis(3-aminopropyl)amine, bis(hexanethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine, based on this core structure. An example is:

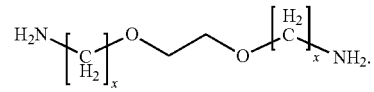

Exemplary polyetheramines include 2,2'-ethylenedioxy)bis (ethylamine) and 4,7,10-trioxa-1,13-tridecanediamine.

Other suitable amines include, but are not limited to, tris(2-aminoethyl)amine, triethylenetetramine, N,N'-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine and 2,4,6-triaminopyrimidine.

Amphoteric amines, i.e., amines that can react as an acid as well as a base, are another class of amines of use in this invention. Examples of amphoteric amines include proteins and amino acids such as gelatin, L-lysine, D-lysine, L-arginine, D-arginine, L-lysine monohydrochloride, D-lysine monohydrochloride, L-arginine monohydrochloride, D-arginine monohydrochloride, L-ornithine monohydrochloride, D-ornithine monohydrochloride or a mixture thereof.

Guanidine amines and guanidine salts are yet another class of amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Commercially available examples of amines include JEFFAMINE EDR-148 (where x=2), JEFFAMINE EDR-176

(where x=3) (from Huntsman). Other polyether amines include the JEFFAMINE ED Series, and JEFFAMINE TRIAMINES.

In general, the range of cross-linking agent concentration or the total amine concentration in the microcapsule composition varies from 5% to 0.1%, preferably from about 3% to about 0.25%, most preferably from about 2 to about 0.5% of the total capsule suspension. In accordance with embodiments including the use of a guanidine amine, a guanidine salt or amphoteric amine, the fragrance emulsion can further include sodium carbonate.

In one embodiment of the invention, the cross linking agent, e.g., hexamethylene diamine, is added to the microcapsule reaction at a temperature of 35° C. In another embodiment, the cross linking agent is added to the microcapsule reaction at a temperature of 22° C.

Capsule Formation Aid.

In another embodiment of the invention, a microcapsule composition is provided that contains an active material that is encapsulated by a polyurea polymer which are reacted in the presence of a capsule formation aid, e.g., a surfactant or dispersant. For the purpose of this invention, capsule formation aids improve the performance of the microcapsule system. Performance is measured by the intensity of the fragrance release during the pre-rub phase and post-rub. The pre-rub phase is the phase when the microcapsules have been deposited on the cloth, e.g., after a fabric softener containing microcapsules has been used during the wash cycle. The post-rub phase is after the microcapsules have been deposited and the capsules are broken by friction or other similar mechanisms.

In some embodiments, the capsule formation aid is a surfactant such as polyvinyl alcohol (PVA), polystyrene sulfonate (PSS), carboxymethyl cellulose (CMC), sodium salt of naphthalene sulfonate condensate, or a mixture thereof. In general, the range of surfactant concentration in the microcapsule composition varies from 5% to 0.1% and preferable from 2% to 0.25%.

Commercially available surfactants include, but are not limited to, sulfonated naphthalene-formaldehyde condensates such as MORWET D425 (Akzo Nobel); partially hydrolyzed polyvinyl alcohols such as MOWIOLs, e.g., MOWIOL 3-83 (Air Products); sulfonated polystyrenes such as FLEXAN II (Akzo Nobel).

Core/Active Materials.

The core of the microcapsules of the invention can include one or more active materials including, but not limited to, flavors and/or fragrance ingredients such as fragrance oils. Individual perfume ingredients that can be included in the capsules of this invention include fragrances containing:

i) hydrocarbons, such as, for example, 3-carene, α-pinene, β-pinene, α-terpinene, γ-terpinene, p-cymene, bisabolene, camphene, caryophyllene, cedrene, farnesene, limonene, longifolene, myrcene, ocimene, valencene, (E,Z)-1,3,5-undecatriene, styrene, and diphenylmethane;

ii) aliphatic alcohols, such as, for example, hexanol, octanol, 3-octanol, 2,6-dimethylheptanol, 2-methyl-2-heptanol, 2-methyl-2-octanol, (E)-2-hexenol, (E)- and (Z)-3-hexenol, 1-octen-3-ol, a mixture of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol, aliphatic aldehydes and their acetals such as for example hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal-diethylacetal, 1,1-dimethoxy-2,2,5-trimethyl-4-hexene, and citronellyl oxyacetaldehyde;

iii) aliphatic ketones and oximes thereof, such as, for example, 2-heptanone, 2-octanone, 3-octanone, 2-nonanone, 5-methyl-3-heptanone, 5-methyl-3-heptanone oxime, 2,4,4,7-tetramethyl-6-octen-3-one, aliphatic sulfur-containing compounds, such as for example 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol, and aliphatic nitriles (e.g., 2-nonenenitrile, 2-tridecenenitrile, 2,12-tridecenenitrile, 3,7-dimethyl-2,6-octadienenitrile, and 3,7-dimethyl-6-octenenitrile);

iv) aliphatic carboxylic acids and esters thereof, such as, for example, (E)- and (Z)-3-hexenylformate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexylbutyrate, (E)- and (Z)-3-hexenyl isobutyrate, hexyl crotonate, ethylisovalerate, ethyl-2-methyl pentanoate, ethyl hexanoate, allyl hexanoate, ethyl heptanoate, allyl heptanoate, ethyl octanoate, ethyl-(E,Z)-2,4-decadienoate, methyl-2-octinate, methyl-2-noninate, allyl-2-isoamyl oxyacetate, and methyl-3,7-dimethyl-2,6-octadienoate;

v) acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

vi) acyclic terpene aldehydes and ketones, such as, for example, geranial, neral, citronellal, 7-hydroxy-3,7-dimethyloctanal, 7-methoxy-3,7-dimethyloctanal, 2,6,10-trimethyl-9-undecenal, α-sinensal, β-sinensal, geranylacetone, as well as the dimethyl- and diethylacetals of geranial, neral and 7-hydroxy-3,7-dimethyloctanal;

vii) cyclic terpene alcohols, such as, for example, menthol, isopulegol, alpha-terpineol, terpinen-4-ol, menthan-8-ol, menthan-1-ol, menthan-7-ol, borneol, isoborneol, linalool oxide, nopol, cedrol, ambrinol, vetiverol, guaiol, and the formates, acetates, propionates, isobutyrates, butyrates, isovalerates, pentanoates, hexanoates, crotonates, tiglinates and 3-methyl-2-butenoates of alpha-terpineol, terpinen-4-ol, methan-8-ol, methan-1-ol, methan-7-ol, borneol, isoborneol, linalool oxide, nopol, cedrol, ambrinol, vetiverol, and guaiol;

viii) cyclic terpene aldehydes and ketones, such as, for example, menthone, isomenthone, 8-mercaptomenthan-3-one, carvone, camphor, fenchone, α-ionone, β-ionone, α-n-methylionone, β-n-methylionone, α-isomethylionone, β-isomethylionone, alpha-irone, α-damascone, β-damascone, β-damascenone, δ-damascone, γ-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H-)-one, nootkatone, dihydronootkatone; acetylated cedarwood oil (cedryl methyl ketone);

ix) cyclic alcohols, such as, for example, 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol;

x) cycloaliphatic alcohols, such as, for example, alpha, 3,3-trimethylcyclo-hexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol;

xi) cyclic and cycloaliphatic ethers, such as, for example, cineole, cedryl methyl ether, cyclododecyl methyl ether;

xii) (ethoxymethoxy)cyclododecane; alpha-cedrene epoxide, 3a,6,6,9a-tetramethyldodecahydronaphtho[2,1-b]furan, 3a-ethyl-6,6,9a-trimethyldodecahydronaphtho[2,1-b]furan, 1,5,9-trimethyl-13-oxabicyclo[10.1.0]-trideca-4,8-diene, rose oxide, 2-(2,4-dimethyl-3-cyclohexen-1-yl)-5-methyl-5-(1-methylpropyl)-1,3-dioxan-;

xiii) cyclic ketones, such as, for example, 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-1-one, 6,7-dihydro-1,1,2,3,3-pentamethyl-4(5H)-indanone, 5-cyclohexadecen-1-one, 8-cyclohexadecen-1-one, 9-cycloheptadecen-1-one, cyclopentadecanone, cycloaliphatic aldehydes, such as, for example, 2,4-dimethyl-3-cyclohexene carbaldehyde, 2-methyl-4-(2,2,6-trimethyl-cyclohexen-1-yl)-2-butenal, 4-(4-hydroxy-4-methylpentyl)-3-cyclohexene carbaldehyde, 4-(4-methyl-3-penten-1-yl)-3-cyclohexene carbaldehyde;

xiv) cycloaliphatic ketones, such as, for example, 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphtalenyl methyl-ketone, methyl-2,6,10-trimethyl-2,5,9-cyclododecatrienyl ketone, tert-butyl-(2,4-dimethyl-3-cyclohexen-1-yl)ketone;

xv) esters of cyclic alcohols, such as, for example, 2-tert-butylcyclohexyl acetate, 4-tert-butylcyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl-isobutyrate, 4,7-methanooctahydro-5 or 6-indenyl acetate;

xvi) esters of cycloaliphatic carboxylic acids, such as, for example, allyl 3-cyclohexyl-propionate, allyl cyclohexyl oxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate;

xvii) aromatic and aliphatic alcohols, such as, for example, benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol;

xviii) esters of aliphatic alcohols and aliphatic carboxylic acids, such as, for example, benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, α-trichloromethylbenzyl acetate, α,α-dimethylphenylethyl acetate, alpha, alpha-dimethylphenylethyl butyrate, cinnamyl acetate, 2-phenoxyethyl isobutyrate, 4-methoxybenzyl acetate, araliphatic ethers, such as for example 2-phenylethyl methyl ether, 2-phenylethyl isoamyl ether, 2-phenylethyl-1-ethoxyethyl ether, phenylacetaldehyde dimethyl acetal, phenylacetaldehyde diethyl acetal, hydratropaaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin;

xix) aromatic and aliphatic aldehydes, such as, for example, benzaldehyde; phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert-butylphenyl)propanal, 3-(4-tert-butylphenyl)propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylene-dioxybenzaldehyde, 3,4-dimethoxybenzaldehyde, 2-methyl-3-(4-methoxyphenyl)propanal, 2-methyl-3-(4-methylendioxyphenyl)propanal;

xx) aromatic and aliphatic ketones, such as, for example, acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methyl-ethyl)-1H-5-indenyl]ethanone, 5',6',7',8'-tetrahydro-3',5',5',6',8',8'-hexamethyl-2-acetonaphthone;

xxi) aromatic and araliphatic carboxylic acids and esters thereof, such as, for example, benzoic acid, phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate;

xxii) nitrogen-containing aromatic compounds, such as, for example, 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenonitrile, 5-phenyl-3-methylpentanonitrile, methyl anthranilate, methy-N-methylanthranilate, Schiff's bases of methyl anthranilate with 7-hydroxy-3,7-dimethyloctanal, 2-methyl-3-(4-tert-butylphenyl)propanal or 2,4-dimethyl-3-cyclohexene carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine;

xxiii) phenols, phenyl ethers and phenyl esters, such as, for example, estragole, anethole, eugenol, eugenyl methyl ether, isoeugenol, isoeugenol methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate;

xxiv) heterocyclic compounds, such as, for example, 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one;

xxv) lactones, such as, for example, 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis- and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene-1,12-dodecanedioate, ethylene-1,13-tridecanedioate, coumarin, 2,3-dihydrocoumarin, and octahydrocoumarin; and xxvi) essential oils, concretes, absolutes, resins, resinoids, balsams, tinctures such as for example ambergris tincture, amyris oil, angelica seed oil, angelica root oil, aniseed oil, valerian oil, basil oil, tree moss absolute, bay oil, armoise oil, benzoe resinoid, bergamot oil, beeswax absolute, birch tar oil, bitter almond oil, savory oil, buchu leaf oil, cabreuva oil, cade oil, calamus oil, camphor oil, cananga oil, cardamom oil, cascarilla oil, cassia oil, cassie absolute, castoreum absolute, cedar leaf oil, cedar wood oil, cistus oil, citronella oil, lemon oil, copaiba balsam, copaiba balsam oil, coriander oil, costus root oil, cumin oil, cypress oil, davana oil, dill weed oil, dill seed oil, eau de brouts absolute, oakmoss absolute, elemi oil, estragon oil, eucalyptus citriodora oil, eucalyptus oil (cineole type), fennel oil, fir needle oil, galbanum oil, galbanum resin, geranium oil, grapefruit oil, guaiacwood oil, gurjun balsam, gurjun balsam oil, helichrysum absolute, helichrysum oil, ginger oil, iris root absolute, iris root oil, jasmine absolute, calamus oil, blue camomile oil, Roman camomile oil, carrot seed oil, cascarilla oil, pine needle oil, spearmint oil, caraway oil, labdanum oil, labdanum absolute, labdanum resin, lavandin absolute, lavandin oil, lavender absolute, lavender oil, lemon-grass oil, lovage oil, lime oil distilled, lime oil expressed, linaloe oil, Litsea cubeba oil, laurel leaf oil, mace oil, marjoram oil, mandarin oil, massoi (bark) oil, mimosa absolute, ambrette seed oil, musk tincture, clary sage oil, nutmeg oil, myrrh absolute, myrrh oil, myrtle oil, clove leaf oil, clove bud oil, neroli oil, olibanum absolute, olibanum oil, opopanax oil, orange flower absolute, orange oil, origanum oil, palmarosa oil, patchouli oil, perilla oil, Peru balsam oil, parsley leaf oil, parsley seed oil, petitgrain oil, peppermint oil, pepper oil, pimento oil, pine oil, pennyroyal oil, rose absolute, rosewood oil, rose oil, rosemary oil, Dalmatian sage oil, Spanish sage oil, sandal-wood oil, celery seed oil: spike-lavender oil, star anise oil, storax oil, tagetes oil, fir needle oil, tea tree oil, turpentine oil, thyme oil, Tolu balsam, tonka bean absolute, tuberose absolute, vanilla extract, violet leaf absolute, verbena oil, vetiver oil, juniperberry oil, wine lees oil, wormwood oil, wintergreen oil, ylang-ylang oil, hyssop oil, civet absolute, cinnamon leaf oil, cinnamon bark oil, and fractions thereof or ingredients isolated therefrom.

In some embodiments, the amount of encapsulated fragrance oil is from about 80% to about 5% of the total capsule suspension, preferably from about 60% to about 10% of the total capsule suspension, and most preferably from about 50% to about 20% of the total capsule suspension.

In addition to the fragrance materials, the present invention also contemplates the incorporation of other core additives including solvent, emollients, and core modifier materials encapsulated by the encapsulating polymer.

The present invention also contemplates the incorporation of solvent materials, particles or polymeric core modifiers into the core. The solvent materials are hydrophobic materials that are miscible in the fragrance materials used in the present invention. Suitable solvents are those having reasonable affinity for the fragrance chemicals and a Clog P greater than 3.3, preferably greater than 6 and most preferably greater that 10. Suitable materials include, but are not limited to triglyceride oil, mono and diglycerides, mineral oil, silicone oil, diethyl phthalate, polyalpha olefins, castor oil and isopropyl myristate. In a highly preferred embodiment the solvent materials are combined with fragrance materials that have high Clog P values as set forth above. It should be noted that selecting a solvent and fragrance with high affinity for each other will result in the most pronounced improvement in stability. This specific affinity may be measured by determining the Solvent-Water partition coefficient for the fragrance material. Appropriate solvents include, but are not limited to, mono-, di- and tri-esters, and mixtures thereof, of fatty acids and glycerine. The fatty acid chain can range from C4-C26. Also, the fatty acid chain can have any level of unsaturation. For instance capric/caprylic triglyceride known as NEOBEE M5 (Stepan Corporation). Other suitable examples are the CAPMUL series by Abitec Corporation, for instance CAPMUL MCM. Isopropyl myristate fatty acid esters of polyglycerol oligomers include $R_2CO$—[$OCH_2$—$CH(OCOR_1)$—$CH2O$—]$_n$, where $R_1$ and $R_2$ can be H or C4-26 aliphatic chains, or mixtures thereof, and n ranges between 2-50, preferably 2-30. Nonionic fatty alcohol alkoxylates like the NEODOL surfactants by BASF, the DOBANOL surfactants by Shell Corporation or the BIOSOFT surfactants by Stepan, wherein the alkoxy group is ethoxy, propoxy, butoxy, or mixtures thereof. In addition, these surfactants can be end-capped with methyl groups in order to increase their hydrophobicity. Di- and tri-fatty acid chain containing nonionic, anionic and cationic surfactants, and mixtures thereof are also contemplated, as are fatty acid esters of polyethylene glycol, polypropylene glycol, and polybutylene glycol, or mixtures thereof. Polyalphaolefins such as the EXXONMOBIL PURESYM PAO line; esters such as the EXXONMOBIL PURESYN esters; mineral oil; silicone oils such polydimethyl siloxane and polydimethylcyclosiloxane; diethyl phthalate; and di-isodecyl adipate can also be included. In certain embodiments, ester oils have at least one ester group in the molecule. One type of common ester oil useful in the present invention are the fatty acid mono and polyesters such as cetyl octanoate, octyl isononanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; sucrose ester and polyesters, sorbitol ester, and the like. A second type of useful ester oil is predominantly composed of triglycerides and modified triglycerides. These include vegetable oils such as jojoba, soybean, canola, sunflower, safflower, rice bran, avocado, almond, olive, sesame, persic, castor, coconut, and mink oils. Synthetic triglycerides can also be employed provided they are liquid at room temperature. Modified triglycerides include materials such as ethoxylated and maleated triglyceride derivatives provided they are liquids. Proprietary ester blends such as those sold by FINETEX as FINSOLV are also suitable, as is ethylhexanoic acid glyceride. A third type of ester oil is liquid polyester formed from the reaction of a dicarboxylic acid and a diol. Examples of polyesters suitable for the present invention are the polyesters marketed by EXXONMOBIL under the trade name PURESYN ESTER.

Nanoscale solid particulate materials such as those disclosed in U.S. Pat. No. 7,833,960 may also be incorporated into the core and may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), magenase (Mn), iron (Fe), nickel (Ni), cobalt (Co), copper (Cu), gold (Au), silver (Ag), platinum (Pt) and palladium (Pd).

Polymer particles of any chemical composition and nature are suitable for the present invention as long as their physical dimension falls into the prescribed region and a liquid core is generated. The polymer particles can be selected from a nonlimiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a non-limiting list including silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, CuO, AgO, $MnO_2$, as well as other transition metal oxides.

Examples of nanoscaled material include AEROSIL R812, which has a particle size of less than 25 nm according to the specification from the manufacture, Degussa Corp. Other suitable materials from Degussa include, but not limited to, AEROSIL R972, AEROSIL R974, AEROSIL R104, AEROSIL R106, AEROSIL R202, AEROSIL R805, AEROSIL R812, AEROSIL R812S, AEROSIL R816, AEROSIL R7200, AEROSIL R9200, and AEROXIDE $TiO_2$ P25, AEROXIDE T805, AEROXIDE LE1, AEROXIDE LE2, AEROXIDE $TiO_2$ NKT 90, AEROXIDE Alu C805, titanium dioxide PF2, SIPERNAT D110, SIPERNAT D-380. The hydrophobic materials from Deguassa Corp. such as including AEROSILE R812 and R972 are especially preferred.

Nanoscaled materials such as UVINUL $TiO_2$ and Z-COTE HP1 manufactured by BASF can also be used as well as and TI-PURE titanium dioxide, TI-PURE R-700, and TI-SELECT. Additional suitable materials include TS-6200 from Dupont and ZEROFREE 516, HUBERDERM 2000 and HUBERDERM 1000 from the J.M. Huber Corporation, Havre De Grace, Md. Silica products such as SYLOID 63, 244, 72, 63FP 244FP, 72FP, SYLOX 15, 2 and Zeolites such as SYLOSIV A3, SYLOSIV A4 and SYLOSIV K300 from Grace Davison can also be used.

Polymeric core modifiers are also contemplated. It has been found that the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion. Polymeric core modifiers include copolymers of ethylene; copolymers of ethylene and vinyl acetate (ELVAX polymers by DOW Corporation); copolymers of ethylene and vinyl alcohol (EVAL polymers by Kuraray); ethylene/acrylic elastomers such as VALNAC polymers by Dupont; polyvinyl polymers, such as polyvinyl acetate; alkyl-substituted cellulose, such as ethyl cellulose (ETHOCEL made by DOW Corporation) and hydroxypropyl celluloses (KLUCEL polymers by Hercules); cellulose acetate butyrate available from Eastman Chemical; polyacrylates (e.g., AMPHOMER, DEMACRYL LT and DERMACRYL 79, made by National Starch and Chemical Company, the AMERHOLD polymers by Amerchol Corporation, and ACUDYNE 258 by ISP Corporation); copolymers of acrylic or methacrylic acid and fatty esters of acrylic or methacrylic acid such as INTELIMER POLYMERS made by Landec Corporation (see also U.S. Pat. Nos. 4,830,855, 5,665,822, 5,783,302, 6,255,367 and 6,492,462); polypropylene oxide; polybutylene oxide of poly(tetrahydrofuran); polyethylene terephthalate; polyurethanes (DYNAM X by National Starch); alkyl esters of poly(methyl vinyl ether); maleic anhydride copolymers, such as the GANTREZ copolymers and OMNIREZ 2000 by ISP Corporation; carboxylic acid esters of polyamines, e.g., ester-terminated polyamides (ETPA) made by Arizona Chemical Company; polyvinyl pyrrolidone (LUVISKOL series of BASF); block copolymers of ethylene oxide, propylene oxide and/or butylenes oxide including, e.g., PLURONIC and SYNPERONIC polymers/dispersants by BASF. Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

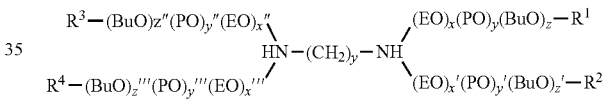

where $R^1$, $R^2$, $R^3$, and $R^4$ are independently H or any alkyl or fatty alkyl chain group. Examples of such polymers are the commercially known as TETRONICS by BASF Corporation.

Sacrificial core ingredients can also be included. These ingredients are designed to be lost during or after manufacture and include, but are not limited to, highly water soluble or volatile materials.

The level of solvent materials, particles or polymeric core modifiers in the core encapsulated by the encapsulating polymer should be greater than about 10 weight percent, preferably greater than about 30 weight percent and most preferably greater than about 70 weight percent. In addition to the solvent, it is preferred that higher Clog P fragrance materials are employed. It is preferred that greater than about 60 weight percent, preferably greater than 80 and more preferably greater than about 90 weight percent of the fragrance chemicals have Clog P values of greater than about 3.3, preferably greater than about 4 and most preferably greater than about 4.5. Those with skill in the art will appreciate that many formulations can be created employing various solvents and fragrance chemicals. The use of a high level of high Clog P fragrance chemicals will likely require a lower level of hydrophobic solvent than fragrance chemicals with lower Clog P to achieve similar performance stability. As those with skill in the art will appreciate, in a highly preferred embodiment, high Clog P fragrance chemicals and hydrophobic solvents comprise greater than about 80, preferably more than about 90 and most preferably greater than 95 weight percent of the fragrance composition. As discussed above, specific Clog P values may be measured between candidate solvents and water for the fragrance materials to be included in the core. In this way, an optimum solvent choice may be made. In fact, since most fragrances will have many ingredients, it may be preferable to measure the partitioning of a specific fragrance blend in solvent and water in order to determine the effect of any material interactions.

Deposition Aids.

Deposition aids can also be used to aid in deposition of capsules to surfaces such as fabric, hair or skin. These include but are not limited to anionically, cationically, non-ionically, Or zwitterionically charged water-soluble polymers which can be applied to the polyurea capsule. This water-soluble polymer can also be an amphoteric polymer with a ratio of cationic and anionic functionalities resulting in a net total charge of zero and positive, i.e., cationic. Those skilled in the art would appreciate that the charge of these polymers can be adjusted by changing the pH, depending on the product in which this technology is to be used. Any suitable method for coating the deposition aids onto the encapsulated fragrance materials can be used. The nature of suitable polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (covalently) grafted to the capsule or particle surface. Chemical modification of the capsule or particle surface is another way to optimize anchoring of the polymer coating to capsule or particle surface. Furthermore, the capsule and the polymer need to want to go to the desired interface and, therefore, need to be compatible with the chemistry (polarity, for instance) of that interface. Therefore, depending on which capsule chemistry and interface (e.g., cotton, polyester, hair, skin, wool), the polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from about 1,000 to about 1000,000,000, preferably from about 5,000 to about 10,000,000. As used herein, molecular weight is provided as weight average molecular weight.

Particular examples of polymers that can be used to coat the polyurea capsule include, e.g., polysaccharides such as guar, alginates, starch, xanthan, chitosan, cellulose, dextrans, arabic gum, carrageenan, and hyaluronates. These polysaccharides can be employed with cationic modification and alkoxy-cationic modifications such as cationic hydroxyethyl or cationic hydroxypropyl. For example, cationic reagents of choice are 3-chloro-2-hydroxypropyl trimethylammonium chloride or its epoxy version. Another example is graft-copolymers of polyDADMAC on cellulose, e.g., CELQUAT L-200 (POLYQUATERNIUM-4), POLYQUATERNIUM-10 and POLYQUATERNIUM-24, commercially available from National Starch, Bridgewater, N.J. Alternatively, polysaccharides can be employed with aldehyde, carboxyl, succinate, acetate, alkyl, amide, sulfonate, ethoxy, propoxy, butoxy, and combinations of these functionalities; or any hydrophobic modification (compared to the polarity of the polysaccharide backbone). The above modifications can be in any ratio and the degree of functionalization can be up to complete substitution of all functionalizable groups, as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified to the backbone. The counterions can be any halide ion or organic counter ion. See U.S. Pat. Nos. 6,297,203 and 6,200,554.

Another source of cationic polymers contain protonatable amine groups so that the overall net charge is zero (amphoteric: mixture of cationic and anionic functional groups) or positive. The pH during use will determine the overall net charge of the polymer. Examples include silk protein, zein, gelatin, keratin, collagen and any polypeptide, such as polylysine.

Further cationic polymers include polyvinyl polymers with up to 5 different types of monomers can be used. The monomers of such polymer have the generic formula:

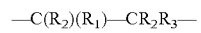

herein, $R_1$ is any alkane from C1-C25 or H, wherein the number of double bonds ranges from 0-5, $R_1$ is an alkoxylated fatty alcohol with any alkoxy carbon-length of C1-C25, or $R_1$ is a liquid crystalline moiety that can provide the polymer with thermotropic liquid crystalline properties $R_2$ is H or $CH_3$; and $R_3$ is —Cl, —$NH_2$ (i.e., polyvinyl amine or its copolymers with N-vinyl formamide.

Such polyvinyl polymers are sold under the name LUPAMIN 9095 by BASF Corporation. Further suitable cationic polymers containing hydroxylalkylvinylamine units, as disclosed in U.S. Pat. No. 6,057,404.

Another class of materials are polyacrylates with up to 5 different types of monomers. Monomers of polyacrylates have the generic formula:

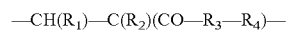

wherein, $R_1$ is any alkane from C1-C25 or H with number of double bonds from 0-5, $R_1$ is an alkoxylated fatty alcohol with a C1-C25 alkyl chain length, or $R_1$ is a liquid crystalline moiety that provides the polymer with thermotropic liquid crystalline properties;

$R_2$ is H or $CH_3$;

$R_3$ is a C1-25 alkyl alcohol or an alkylene oxide with any number of double bonds, or $R_3$ may be absent such that the C═O bond is (via the C-atom) directly connected to $R_4$; and $R_4$ can be —$NH_2$, —$NHR_1$, —$NR_1R_2$, —$NR_1R_2R_6$ (where $R_6$=$R_1$, $R_2$, or —$CH_2$—COOH or its salt), —NH—C(O)—, sulfobetaine, betaine, polyethylene oxide, poly(ethyleneoxide/propylene oxide/butylene oxide) grafts with any end group, H, OH, styrene sulfonate, pyridine, quaternized pyridine, alkyl-substituted pyrrolidone or pyridine, pyridine-N-oxide, imidazolinium halide, imidazolium halide, imidazol, piperidine, —$OR_1$, —OH, —COOH alkali salt, sulfonate, ethoxy sulphate, pyrrolidone, caprolactam, phenyl-$R_4$ or naphthalene-$R_5$, where $R_4$ and $R_5$ are $R_1$, $R_2$, $R_3$, sulfonic acid or its alkali salt or organic counter ion. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC). DMAEMA can be found in GAFQUAT and GAFFIX VC-713 polymers from ISP. MAPTAC can be found in BASF's LUVIQUAT PQ11 PN and ISP's GAFQUAT HS100.

Another group of polymers that can be used are those that contain cationic groups in the main chain or backbone. Included in this group are:

i) polyalkylene imines such as polyethylene imine, commercially available as LUPASOL from BASF. Any molecular weight and any degree of crosslinking of this polymer can be used in the present invention;

ii) ionenes as disclosed in U.S. Pat. No. 4,395,541 and U.S. Pat. No. 4,597,962;

iii) adipic acid/dimethyl amino hydroxypropyl diethylene triamine copolymers, such as CARTARETIN F-4 and F-23, commercially available from Sandoz;

iv) polymers of the general formula: $-[N(CH_3)_2-(CH_2)_x-NH-(CO)-NH-(CH_2)_y-N(CH_3)_2-(CH_2)_z-O-(-CH_2)_p]_n-$, with x, y, z, p=1-12, and n according to the molecular weight requirements. Examples are Polyquaternium 2 (MIRAPOL A-15), Polyquaternium-17 (MIRAPOL AD-1), and Polyquaternium-18 (MIRAPOL AZ-1). Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e., Polyquaternium-80). Silicones with general structure: $-Si(R_1)(R_2)-O-]_x-[Si(R_3)(R_2)-O-]_y-$ where $R_1$ is any alkane from C1-C25 or H with number of double bonds from 0-5, aromatic moieties, polysiloxane grafts, or mixtures thereof. $R_1$ can also be a liquid crystalline moiety that can provide the polymer with thermotropic liquid crystalline properties. $R_2$ can be H or $CH_3$; and $R_3$ can be $-R_1-R_4$, where $R_4$ can be $-NH_2$, $-NHR_1$, $-NR_1R_2$, $-NR_1R_2R_6$ (where $R_6=R_1$, $R_2$, or $-CH_2-COOH$ or its salt), $-NH-C(O)-$, $-COOH$, $-COO-$ alkali salt, any C1-25 alcohol, $-C(O)-NH_2$ (amide), $-C(O)-N(R_2)(R_2')(R_2'')$, sulfobetaine, betaine, polyethylene oxide, poly(ethyleneoxide/propylene oxide/butylene oxide) grafts with any end group, H, $-OH$, styrene sulfonate, pyridine, quaternized pyridine, alkyl-substituted pyrrolidone or pyridine, pyridine-N-oxide, imidazolinium halide, imidazolium halide, imidazol, piperidine, pyrrolidone, caprolactam, sulfonate, ethoxysulphate phenyl-$R_5$ or naphthalene-$R_6$ where $R_5$ and $R_6$ are $R_1$, $R_2$, $R_3$, sulfonic acid or its alkali salt or organic counter ion. $R_3$ can also be $-(CH_2)_x-O-CH_2-CH(OH)-CH_2-N(CH_3)_2-CH_2-COOH$ and its salts. Any mixture of these $R_3$ groups can be selected. X and y can be varied as long as the theoretical net charge of the polymer is zero (amphoteric) or positive. In addition, polysiloxanes containing up to 5 different types of monomeric units may be used. Examples of suitable polysiloxanes are found in U.S. Pat. Nos. 4,395,541 4,597,962 and 6,200,554. Another group of polymers that can be used to improve capsule/particle deposition are phospholipids that are modified with cationic polysiloxanes. Examples of these polymers are found in U.S. Pat. No. 5,849,313, WO Patent Application 95/18096A1 and European Patent EP0737183B1.

Furthermore, copolymers of silicones and polysaccharides and proteins can be used (e.g., those commercially available as CRODASONE brand products).

Another class of polymers includes polyethylene oxide-co-propyleneoxide-co-butylene oxide polymers of any ethylene oxide/propylene oxide/butylene oxide ratio with cationic groups resulting in a net theoretical positive charge or equal to zero (amphoteric). Examples of such polymers are the commercially available TETRONIC brand polymers.

Suitable polyheterocyclic (the different molecules appearing in the backbone) polymers include the piperazine-alkylene main chain copolymers disclosed by Kashiki and Suzuki (1986) *Ind. Eng. Chem. Fundam.* 25:120-125.

As indicated, the addition of hydrophobic polymers to the core can also improve stability by slowing diffusion of the fragrance from the core. The level of polymer is normally less than 80% of the core by weight, preferably less than 50%, and most preferably less than 20%. The basic requirement for the polymer is that it be miscible or compatible with the other components of the core, namely the fragrance and other solvent. Preferably, the polymer also thickens or gels the core, thus further reducing diffusion.

In accordance with the compositions and methods disclosed herein, the wall polymer level of the polyurea capsules can be from about 15 to about 0.1% of the total capsule suspension, preferably from about 10 to about 1% of the total capsule suspension, or most preferably from about 5 to about 2% of the total capsule suspension.

In a further embodiment of the invention, the amount of encapsulated active material is from about 80 to about 5% of the total capsule suspension, preferably from about 60% to about 10% of the total capsule suspension, or most preferably from about 50 to about 20% of the total capsule suspension.

In one embodiment of the method, the cross-linking agent is a polyamine, wherein the stoichiometry of the polyamine and polyisocyanate can be manipulated to give reduced amounts of polyisocyanate in the prepared capsule slurry. The stoichiometry of the polyamine to isocyanate will vary from 1 to 1, (one amine group per one isocyanate group), preferably from 2 to 1, (two amine groups per one isocyanate group), and most preferably from 4 to 1 (four amine groups per one isocyanate group).

In certain embodiments of the invention, the capsule slurry is cured at a temperature greater than about 55° C.; greater than about 65° C.; greater than about 75° C.; greater than about 85° C.; greater than about 95° C.; greater than about 105° C. or greater than 120° C.

In accordance with certain embodiments, a curing catalyst is further included in the preparation of the polyurea capsules of this invention. Such curing catalysts include, but are not limited to, Crystalline DABCO (1,4-diazabicyclo[2.2.2]octane).

Microcapsules prepared in accordance with this invention preferably have a size in the range of from 0.1 to 100 microns, or preferably from 0.2 to 50 microns depending on the emulsifier and shear rates used.

Applications.

The present invention is well-suited for use in consumer products including, without limitation, personal care products such as shampoos, rinses, hair conditioners, creams, body washes, body soap, body liquid detergent, or other hygiene product; leave-on personal care applications including hair refresher and lotions; personal cleaners or sanitizers; or fabric care products such as fabric refreshers. Rinse off products may be liquids, solids, pastes, or gels, of any physical form. Also included in the use of the microcapsules are applications where a second active ingredient is included to provide additional benefits for an application. The additional beneficial ingredients include fabric softening ingredients, skin moisturizers, sunscreen, insect repellent and other ingredients as may be helpful in a given application. Also included are the beneficial agents alone, that is without the fragrance.

Capsules having a polyurea capsule wall are very suitable to carry a variety of hydrophobic or hydrophilic benefit agents to be used in products for application to all kinds of surfaces. On the one hand surfaces may be inanimate, such as hard surfaces found in and around the house, e.g., wooden, metal, ceramic, glass and paint surfaces, or soft surfaces such as clothing, carpets, curtains and other textiles. On the other hand, such surfaces may be animate surfaces, more particularly surfaces of a human or animal body, i.e., human or animal skin and hair. For the purposes of this invention animate surfaces do not include plant surfaces.

Products intended for application to a surface are generally intended for washing/cleaning or for caring/protecting or both. Examples are cleaning products for hard surfaces or textiles, caring/protection products like polishes and waxes for delicate surfaces such as wood, car paint and leather, laundry softening agents, anti-soiling agents, water repelling agents, and the like. Examples of products intended for the human skin are bath and shower products and shampoo for skin and hair cleansing, and all kinds of skin and hair care/protection products such as hair conditioners, hand and body lotions and creams, deodorants and antiperspirants, make up products and the like.

The dosage of the microcapsules in the rinse off products is from about 0.05 weight percent to 10 weight percent, preferred 0.2 weight percent to about 5 weight percent, and most preferred 0.5 weight percent to about 2 weight percent.

Cleaning and cleansing compositions will include one or more surfactants that may be chosen from anionic, cationic, nonionic, zwitterionic and amphoteric surfactants known in the art. For cleansing composition for skin or hair the surfactants must obviously meet the condition of being suitable for topical application.

The compositions according to the invention may optionally include a variety of components known in the art and adapted to their specific use. Thus, compositions intended for inanimate surfaces may include components such as builders, sequestrants, hydrotropes, organic solvents, pH regulation components such as organic or inorganic acids and/or bases, thickening agents, chlorine or peroxide bleaches, laundry softening agents, scouring agents, biocides, coloring agents, pearlescent, preservatives, perfumes. Compositions intended for application may contain a variety of vehicles suitable for topical application and a variety of benefit agents for skin or hair.

As described herein, the polyurea capsules of the invention are well-suited for use in a variety of well-known personal and household products such as laundry detergent and fabric softeners, liquid dish detergents, automatic dish detergents, bathroom cleaners, bath tissue, tumble dryer sheets, rug deodorizers, candles, floor cleaners, disinfectants, window cleaners; household devices such as paper towels, disposable wipes, room deodorizers; baby care products such as diaper rash cream/balm or baby powder; baby care devices such as diapers, bibs and wipes; health care devices such as dental floss, toothbrushes, tampons and feminine napkins; personal care products such as personal cleansers (e.g., bar soap or body wash), sunscreen (spray or lotion), wax-based deodorant, glycol/soap-type deodorant, lotion, body powder, shaving cream, bath soak, exfoliating scrub; personal care devices such as facial tissues, and cleansing wipes; hair care products such as shampoo (liquid or dry powder), hair conditioner (rinse out or leave-in), hair fixative or style aids, hair bleaches, dyes or colorants; and beauty care products such as fine fragrances, solid perfume, liquid or powder foundation, eye shadow, and lipstick/lip balm.

These products can employ surfactant and emulsifying systems that are well-known. For example, fabric softener systems are described in U.S. Pat. No. 6,335,315, U.S. Pat. No. 5,674,832, U.S. Pat. No. 5,759,990, U.S. Pat. No. 5,877,145, U.S. Pat. No. 5,574,179; U.S. Pat. No. 5,562,849, U.S. Pat. No. 5,545,350, U.S. Pat. No. 5,545,340, U.S. Pat. No. 5,411,671, U.S. Pat. No. 5,403,499, U.S. Pat. No. 5,288,417, U.S. Pat. No. 4,767,547, and U.S. Pat. No. 4,424,134. Liquid dish detergents are described in U.S. Pat. No. 6,069,122 and U.S. Pat. No. 5,990,065; automatic dish detergent products are described in U.S. Pat. No. 6,020,294, U.S. Pat. No. 6,017,871, U.S. Pat. No. 5,968,881, U.S. Pat. No. 5,962,386, U.S. Pat. No. 5,939,373, U.S. Pat. No. 5,914,307, U.S. Pat. No. 5,902,781, U.S. Pat. No. 5,705,464, U.S. Pat. No. 5,703,034, U.S. Pat. No. 5,703,030, U.S. Pat. No. 5,679,630, U.S. Pat. No. 5,597,936, U.S. Pat. No. 5,581,005, U.S. Pat. No. 5,559,261, U.S. Pat. No. 4,515,705, U.S. Pat. No. 5,169,552, and U.S. Pat. No. 4,714,562. Liquid laundry detergents which can use the present invention include those systems described in U.S. Pat. No. 5,929,022, U.S. Pat. No. 5,916,862, U.S. Pat. No. 5,731,278, U.S. Pat. No. 5,565,145, U.S. Pat. No. 5,470,507, U.S. Pat. No. 5,466,802, U.S. Pat. No. 5,460,752, U.S. Pat. No. 5,458,810, U.S. Pat. No. 5,458,809, U.S. Pat. No. 5,288,431, U.S. Pat. No. 5,194,639, U.S. Pat. No. 4,968,451, U.S. Pat. No. 4,597,898, U.S. Pat. No. 4,561,998, U.S. Pat. No. 4,550,862, U.S. Pat. No. 4,537,707, U.S. Pat. No. 4,537,706, U.S. Pat. No. 4,515,705, U.S. Pat. No. 4,446,042, and U.S. Pat. No. 4,318,818. Shampoo and conditioners that can employ the present invention include those described in U.S. Pat. No. 6,162,423, U.S. Pat. No. 5,968,286, U.S. Pat. No. 5,935,561, U.S. Pat. No. 5,932,203, U.S. Pat. No. 5,837,661, U.S. Pat. No. 5,776,443, U.S. Pat. No. 5,756,436, U.S. Pat. No. 5,661,118, U.S. Pat. No. 5,618,523, U.S. Pat. No. 5,275,755, U.S. Pat. No. 5,085,857, U.S. Pat. No. 4,673,568, U.S. Pat. No. 4,387,090 and U.S. Pat. No. 4,705,681. Toothpastes and other oral care products that can employ the present invention include those described in U.S. Pat. No. 6,361,761, U.S. Pat. No. 6,616,915, U.S. Pat. No. 6,696,044, U.S. Pat. No. 6,193,956, U.S. Pat. No. 6,132,702, U.S. Pat. No. 6,004,538, U.S. Pat. No. 5,939,080, U.S. Pat. No. 5,885,554, U.S. Pat. No. 6,149,894, U.S. Pat. No. 5,505,933, U.S. Pat. No. 5,503,823, U.S. Pat. No. 5,472,685, U.S. Pat. No. 5,300,283 and U.S. Pat. No. 6,770,264.

Personal care products, including cosmetic or pharmaceutical preparations can be formulated as "water-in-oil" (W/O) type emulsions, "oil-in-water" (O/W) type emulsions or as multiple emulsions, for example of the water-in-oil-in-water (W/O/W) type, as a PIT emulsion, a Pickering emulsion, a micro-emulsion or nano-emulsion. Emulsions that are particularly preferred are of the "oil-in-water" (O/W) type or water-in-oil-in-water (W/O/W) type.

As used herein stability of the products is measured at room temperature or above over a period of at least a week. More preferably the capsules of the present invention are allowed to be stored at room temperature for more than about two weeks and preferably more than about a month.

Other active materials that can be included the in polyurea capsules of this invention include antimicrobial agents such as thymol, 2-hydroxy-4,2,4-trichlorodiphenylether, triclocarban; organic sunscreen actives such as oxybenzone, octylmethoxy cinnamate, butylmethoxy dibenzoyln ethane, p-aminobenzoic acid and octyl dimethyl-p-aminobenzoic acid; vitamins such as Vitamin A, Vitamin C and Vitamin E or esters thereof; and malodor counteracting ingredients including, but not limited to, an $\alpha,\beta$-unsaturated carbonyl compounds including but not limited to those disclosed in U.S. Pat. No. 6,610,648 and EP 2,524,704, amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, isomers of bicyclo[2.2.1]hept-5-ene-2-carboxylic acid, ethyl ester, and zinc undecenylate.

These and additional modifications and improvements of the present invention may also be apparent to those with ordinary skill in the art. The particular combinations of elements described and illustrated herein are intended only to represent only a certain embodiment of the present invention and are not intended to serve as limitations of alternative articles within the spirit and scope of the invention. As used herein all percentages are weight percent unless otherwise noted, ppm is understood to stand for parts per million, mL is understood to be milliliter, g is understood to be gram, and mol is understood to be mole. All materials are reported in weight percent unless noted otherwise. As used herein all percentages are understood to be weight percent. The abbreviations PU stand for polyurea and CMC stands for carboxymethyl cellulose.

The invention is described in greater detail by the following non-limiting examples.

Example 1: Polyurea Capsules Prepared With Aliphatic/Aromatic Polyisocyanate and Guanidine Amines/Salts Sample 1: Polyurea Capsule.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of MOWIOL 3-83 (Kuraray America Inc., Houston, Tex.) was mixed with deionized (DI) water (30 g) to form the aqueous phase. The oil phase was then emulsified into the aqueous phase under shearing (ULTRA TURRAX, T25 Basic, and IKA WERKE) at 6500 rpm for two minutes to form the fragrance emulsion.

The fragrance emulsion was placed in a round bottom vessel and 10.4 g of 36% guanidine carbonate (Sigma-Aldrich, St. Louis, Mo.) was added slowly under constant mixing with an overhead mixer. Formation of capsule was immediately visible by optical microscopy. The mixer speed was reduced after the addition of guanidine carbonate was complete. The capsule slurry was cured at 75° C. for three hours.

Sample 2: Polyurea Capsules with a Mixture of Nonionic and Anionic Dispersants.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of MOWIOL 3-83 (Kuraray America Inc., Houston, Tex.) was mixed with a solution (30 g) of 1% CMC in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was placed in a round bottom vessel and 10.4 g of 36% guanidine carbonate (Sigma-Aldrich, St. Louis, Mo.) was added slowly under constant mixing with an overhead mixer. Formation of capsule was immediately visible by optical microscopy. The mixer speed was reduced after the addition of guanidine carbonate was complete. The capsule slurry was cured at 75° C. for three hours.

Sample 3: Polyurea Capsules with a Mixture of Nonionic and Anionic Dispersants and a Catalyst.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of MOWIOL 3-83 (Kuraray America Inc., Houston, Tex.) was mixed with a solution (30 g) of 1% CMC in DI water to form the aqueous phase. The oil phase was then emulsified into the aqueous phase under shearing (ULTRA TURRAX, T25 Basic, and IKA WERKE) at 6500 rpm for two minutes to form the fragrance emulsion.

The fragrance emulsion was heated to 35° C. before drop-wise addition of guanidine carbonate (10.1 g, 36%) and 0.30 g of Crystalline DABCO (1,4-diazabicyclo[2.2.2]octane). Capsules formed immediately after the addition of guanidine carbonate. The capsule slurry was transferred into a round bottom vessel and cured at 75° C. for three hours.

Sample 4: Polyurea Capsules Prepared with DESMODUR 3600, a Mixture of Nonionic and Anionic Dispersants and a Catalyst.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR 3600 (Bayer Corp., Pittsburgh, Pa.) to form the oil phase. In a separate beaker, a solution (130 g) containing 1.0% of MOWIOL 3-83 (Kuraray America Inc., Houston, Tex.) was mixed with a solution (30 g) of 1% CMC in DI water to form the aqueous phase. The oil phase was then emulsified into the aqueous phase under shearing (ULTRA TURRAX, T25 Basic, and IKA WERKE) at 6500 rpm for two minutes to form the fragrance emulsion.

The fragrance emulsion was heated to 35° C. before drop-wise addition of guanidine carbonate (10.1 g, 36%) and 0.30 g of Crystalline DABCO. Capsules formed immediately after the addition of guanidine carbonate. The capsule slurry was transferred into a round bottom vessel and cured at 75° C. for three hours.

Sample 5: Polyurea Capsules Prepared with LUPRANATE M20, a Mixture of Nonionic and Anionic Dispersants, and a Catalyst.

Ninety-six grams of a fragrance, Greenfields (IFF, Union Beach, N.J.) was weighed out and combined with 24 g of NEOBEE oil (Stepan, Chicago, Ill., USA) and 9.6 g of isocyanate monomer, LUPRANATE M20 (BASF Corp., Wyandotte, Mich.) to form the oil phase. In a separate beaker, a solution (130 g) containing 1.0% of MOWIOL 3-83 (Kuraray America Inc., Houston, Tex.) was mixed with a solution (30 g) of 1% CMC in DI water to form the aqueous phase. The oil phase was then emulsified into the aqueous phase under shearing (ULTRA TURRAX, T25 Basic, and IKA WERKE) at 6500 rpm for two minutes to form the fragrance emulsion.

The fragrance emulsion was heated to 35° C. before drop-wise addition of guanidine carbonate (10.1 g, 36%) and 0.30 g of Crystalline DABCO. Capsules formed immediately after the addition of guanidine carbonate. The capsule slurry was transferred into a round bottom vessel and cured at 75° C. for three hours.

Sample 6: Polyurea Capsules Containing a Blend of Nonionic and Cationic Dispersants.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 0.6% of MOWIOL 18-88 (Kuraray America Inc., Houston, Tex.) was mixed with a solution (7.5 g) of 1% LUVIQUAT Ultra Care (polyquaternium-44, BASF, Tarrytown, N.Y.) in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of guanidine carbonate (10.1 g, 36%) and 0.30 g of Crystalline DABCO. Capsules formed immediately after the addition of guanidine carbonate. The capsule slurry was transferred into a round bottom vessel and cured at 75° C. for three hours.

Sample 7: Polyurea Capsules Containing Guanidine Hydrochloride.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of PVA (polyvinyl alcohol, MOWIOL 3-83, (Kurray, Houston, Tex.) was mixed with a solution (30 g) of 1% CMC in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of guanidine hydrochloride (10.1 g, 36%) and 0.30 g of Crystalline DABCO. Capsules formed immediately after the addition of guanidine hydrochloride. The capsule slurry was transferred into a round bottom vessel and cured at 75° C. for three hours.

Sample 8: Polyurea Capsules Containing Guanidine Hydrochloride Prepared Under Basic Conditions.

Ninety-six grams of a fragrance, Greenfields (International IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% PVA (polyvinyl alcohol, MOWIOL 3-83, (Kurray, Houston, Tex.) was mixed with a solution (30 g) of 1% CMC in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

A mixture of guanidine hydrochloride (10.1 g, 36%) and catalyst (0.30 g), Crystalline DABCO (Dow Chemical, Midland, Mich.) was adjusted to pH 12 using 12 mol/L sodium hydroxide. The fragrance emulsion was heated to 35° C. before drop-wise addition of the aqueous mixture. Capsules formed immediately after the addition of guanidine hydrochloride. The capsule slurry was transferred into a round bottom vessel and cured at 75° C. for three hours.

Sample 9: Polyurea Capsules Containing Guanidine Hydrochloride and Sodium Carbonate Prepared Under Basic Conditions.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% PVA (polyvinyl alcohol, MOWIOL 3-83, (Kurray, Houston, Tex.) was mixed with a solution (30 g) of 1% CMC in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

A mixture containing guanidine hydrochloride (10.1 g, 36%), sodium carbonate (3 g), and catalyst (0.30 g), Crystalline DABCO (Dow Chemical, Midland, Mich.) was adjusted to pH 12 by 12 mol/L sodium hydroxide. The fragrance emulsion was heated to 35° C. before drop-wise addition of the aqueous mixture. Capsules formed immediately after the addition of guanidine hydrochloride. The capsule slurry was transferred into a round bottom vessel and cured at 75° C. for two hours.

Physical Characterization of Polyurea Capsule.

Figure 1B:
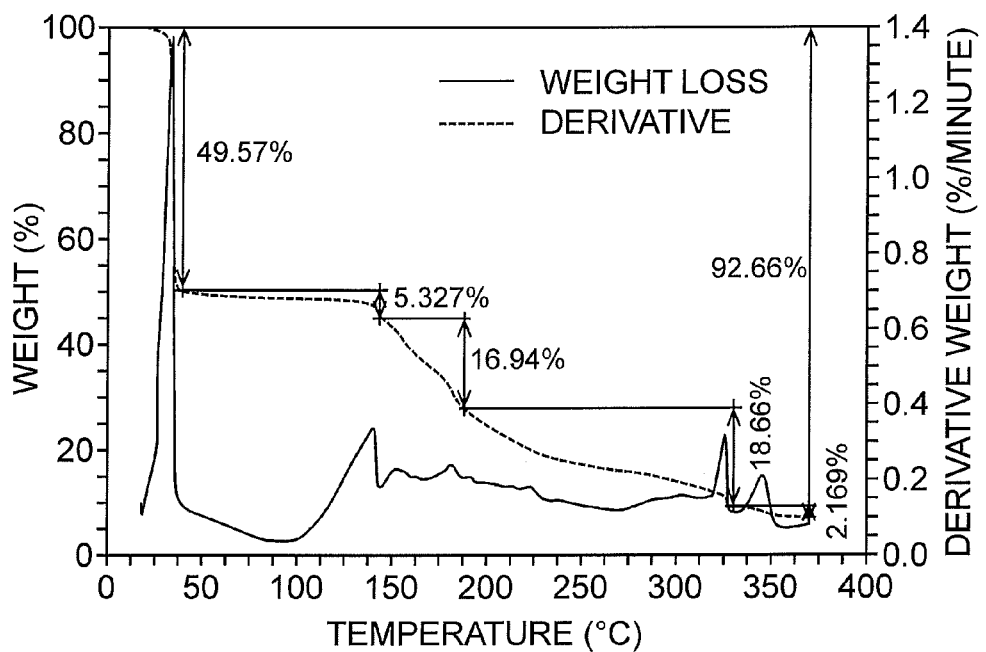
Figure 1C:
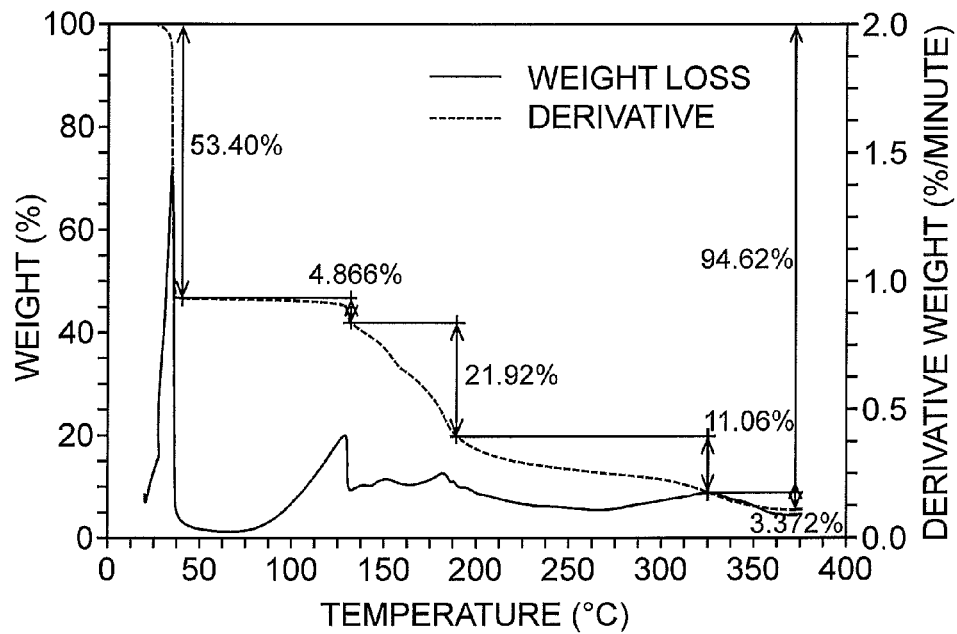
Figure 1D:
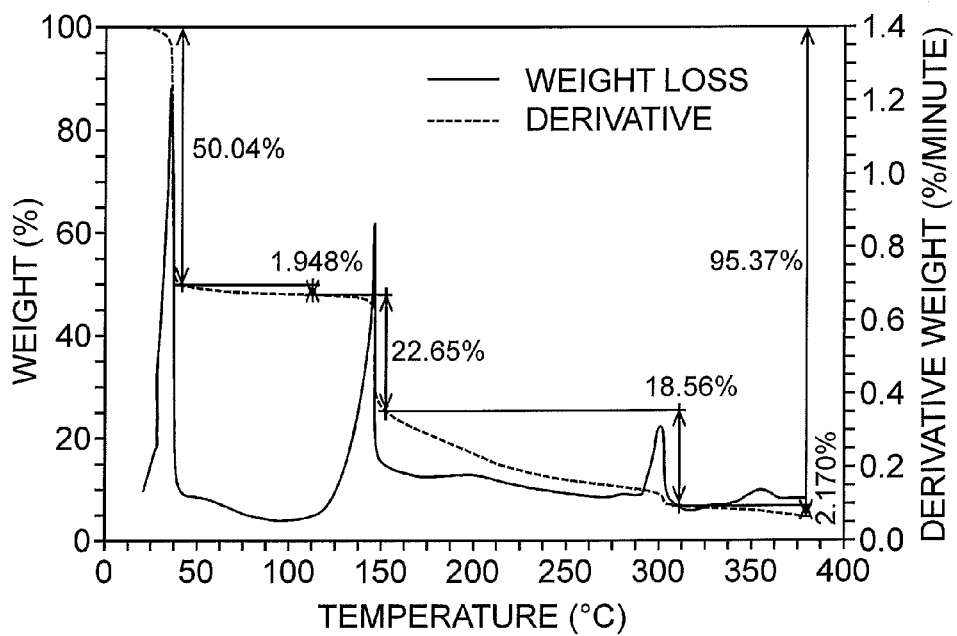

Microscopic analysis indicated that the capsules prepared in accordance with this invention had robust mechanical stability. Furthermore, thermogravimetric analyses (FIGS. 1A-1D) indicated that samples prepared with a mixture of PVA and CMC as capsule formation aid (FIGS. 1A and 1D) released their contents at a higher temperature than capsules made from a mixture of PVA and POLYQUATERNIUM-44 (FIG. 1B) or PVA alone (FIG. 1C). These results demonstrate the thermal stability of the samples prepared with a capsule formation aid.

Encapsulation Performance of Polyurea Capsules.

Sample 2 was diluted with distilled water to yield a mixture containing 0.2% capsule slurry. One gram each of the diluted capsule slurry was directly applied to each side of a 4×6 fabric swatch. Two samples were prepared. The swatches were air-dried overnight and the headspace of the fabrics was analyzed before and after stirring with stainless steel ball bearings to rupture intact capsules. The results of this analysis are presented in Table 1.

TABLE 1

|  | Unstirred | Stirred |
|---|---|---|
| Headspace | 3746 | 16556 |
| Ratio Stirred/Unstirred | — | 4.11 |

This analysis indicated that there was a dramatic increase in headspace after the capsules were disrupted by milling. This demonstrated that increased perfumery perception can be achieved once the capsules are deposited on fabric and ruptured by physical forces.

Sensory Performance of Polyurea Capsules.

To establish the consumer benefits of the polyurea capsules, a capsule slurry was blended into a roll-on base and evaluated for its consumer benefits. The fragrance load was 0.50% neat equivalent. For comparison, a similar solution was prepared using neat fragrance at 0.5%. The sample (0.3 g) was then applied to a blotter (4×6) and was allowed to dry overnight before being evaluated by a panel of 12 judges. The fragrance intensity was rated on a scale ranging from 0 to 10. A numerical value of 10 would suggest the subject generated a strong smell. The results of this analysis are presented in Table 2.

TABLE 2

| Samples | Pre-rubbing intensity | Post-rubbing intensity | $I_{post,capsule}/I_{post,neat}$ |
|---|---|---|---|
| Neat | 1.7 | 2.7 | |
| Capsule Slurry | 1 | 6.1 | 2.25 |

This analysis indicated that the capsules prepared in accordance with the present invention had a much stronger fragrance intensity compared with neat fragrance in the post-rubbing stage and was able to deliver the full benefit of the fragrance formulation.

Perfumery Performance of Polyurea Capsules.

To establish the performance of the polyurea capsules, Samples and 4 were blended into a model rinse conditioner solution that contained 24% cationic surfactant. The fragrance load was 0.5% neat equivalent. For comparison, a similar solution was prepared using neat fragrance at 1%. The perfumery benefit of the capsules was evaluated by conducting a laundry experiment using conventional experimental protocols. Terry towels were used for the washing experiments and were air-dried overnight before being evaluated by a panel of 12 judges. The fragrance intensity was rated on a scale ranging from 0 to 10. A numerical value of 2 would suggest the fabric only produced very week intensity while a value of 10 indicated the subject generated a strong smell. The results of this analysis are presented in Table 3.

TABLE 3

| Samples | Pre-rubbing intensity | Post-rubbing intensity | $I_{pre,capsule}/I_{pre,neat}$ | $I_{post,capsule}/I_{post,neat}$ |
|---|---|---|---|---|
| Neat | 0.5 | 1.5 | | |
| Sample 3 | 1 | 6 | 2 | 4 |
| Sample 4 | 1 | 6.5 | 2 | 4.3 |

This analysis indicated that the polyurea fragrance capsules produced much greater fragrance intensity at the pre-rubbing and post-rubbing stages. The increase in fragrance intensity was much more pronounced in the post-rubbing stage. This demonstrates that the polyurea fragrance capsules prepared in accordance with the current invention are able to retain the fragrance effectively and are capable of delivering the full consumer benefits of the fragrance products.

Application Benefit of Polyurea Capsules.

Application benefit in a personal care product was further evaluated using a hair conditioner formulation. To conduct the experiment, the capsule slurry was dispersed in a hair conditioner base at 0.5% neat fragrance equivalent. The hair conditioner base was a Magick Botanicals oil-free conditioner base. To the base was added Sample 3. The formulation was applied to bundles of hair (40 g each), which contained four hair strands. The bundles were subsequently washed by wetting two bundles (8 strands) under water (water temperature: 100 F/38 C; flow rate: 1 gallon/minute) and lightly squeezing off the excess water. The hair was placed onto a balance and 2 g of unfragranced shampoo was directly applied onto the wet hair. The hair was lathered between palms, 10× clockwise and 10× counterclockwise, keeping the wax part of the swatches between two fingers (not to spread wax over surface of hair). The hair swatches were allowed to stand for 15 seconds and subsequently rinsed under a stream of water for 45 seconds. The process was repeated with hair conditioner. Excess water was gently squeezed out and the hair was allowed to dry overnight. The dried samples were then evaluated by 16 trained panelists and the results are presented in Table 4.

TABLE 4

| Samples | Pre-rubbing intensity | Post-rubbing intensity | $I_{pre,capsule}/I_{pre,neat}$ | $I_{post,capsule}/I_{post,neat}$ |
|---|---|---|---|---|
| Neat | 1.0 | 0.8 | | |
| Sample 3 | 0.5 | 4.0 | 0.5 | 5.0 |

This analysis demonstrated that the product containing polyurea capsules had much stronger perfumery intensity than the neat fragrance. Thus, the polyurea capsule delivered excellent consumer benefits both in the pre- and post-rubbing stage.

Example 2: Polyurea Capsule Prepared With Polyaliphatic Isocyanate and Amphoteric Amines Sample 1: Preparation of Polyurea Capsule.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a 1.0% surfactant solution (160 g) was prepared by dissolving a sufficient amount of MORWET D-425 (Akzo Nobel, Fort Worth, Tex.) in DI water. The oil phase was then emulsified into the aqueous phase under shearing (ULTRA TURRAX, T25 Basic, and IKA WERKE) at 6500 rpm for two minutes to form the fragrance emulsion.

The fragrance emulsion was placed in a round bottom vessel and 10.4 g of 56% lysine (Sigma-Aldrich, St. Louis, Mo.) was added under constant mixing with an overhead mixer. Formation of capsule was immediately visible by optical microscopy. The mixer speed was reduced after the addition of lysine was complete. The capsule slurry was cured at 55° C. temperature for three hours.

Sample 2: Polyurea Capsules Prepared With a Catalyst.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of FLEXAN II (Akzo Nobel, Bridgewater, N.J.) was mixed with a solution (30 g) of 1% CMC in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of a mixture containing lysine (10.1 g, 58%) and Crystalline DABCO (0.30 g, Dow Chemical, Midland, Mich.). Capsules were formed was immediately after the addition of lysine and catalyst. The capsule slurry was transferred into a round bottom vessel and the capsules were cured at 55° C. for 2 hours.

Sample 3: Polyurea capsule Prepared With More Amino Acid.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a 1.0% surfactant solution (160 g) was prepared by dissolving sufficient amount of MORWET D-425 (Akzo Nobel, Fort Worth, Tex.) in DI water. The oil phase was then emulsified into the aqueous phase under shearing (ULTRA TURRAX, T25 Basic, IKA WERKE) at 6500 rpm for two minutes to form the fragrance emulsion.

The fragrance emulsion was placed in a round bottom vessel and 19.8 g of 57% lysine (Sigma-Aldrich, St. Louis, Mo.) and 0.60 g Crystalline DABCO were added under constant mixing with an overhead mixer. Formation of capsule was immediately visible by optical microscopy. The mixer speed was reduced after the addition of lysine was complete. The capsule slurry was cured at 55° C. temperature for three hours.

Sample 4: Polyurea Capsule Prepared with the Addition of Amino Acid at Elevated Temperature.

Ninety six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a 1.0% surfactant solution (160 g) was prepared by dissolving sufficient amount of MORWET D-425 (Akzo Nobel, Fort Worth, Tex., USA) in DI water. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of lysine (10.1 g, 58%) and 0.30 g of Crystalline DABCO. Formation of capsule was immediately visible by optical microscopy. The capsule slurry was transferred into a round bottom vessel and cured at 55° C. temperature for two hours.

Sample 5: Polyurea Capsule Prepared With the Addition of Amino Acid at Elevated Temperature and Curing at Elevated Temperature.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a 1.0% surfactant solution (160 g) was prepared by dissolving a sufficient amount of MORWET D-425 (Akzo Nobel, Fort Worth, Tex.) in DI water. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of lysine (10.1 g, 58%) and 0.30 g of Crystalline DABCO. Formation of capsule was immediately visible by optical microscopy. The capsule slurry was transferred into a round bottom vessel and the capsule slurry was cured at 55° C. for 2 hours and then at 80° C. for 2 hours.

Sample 6: Polyurea Capsules Prepared With a Blend of Dispersants.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% of FLEXAN II (Akzo Nobel, Bridgewater, N.J.) was mixed with a solution (30 g) of 1% CMC in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of lysine (10.1 g, 58%) and 0.30 g of Crystalline DABCO. Formation of capsule was immediately visible by optical microscopy. The capsule slurry was transferred into a round bottom vessel and cured at 55° C. for 2 hours.

Sample 7: Polyurea Capsules Prepared with Arginine.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (120 g) containing 1.1% of FLEXAN II (Akzo Nobel, Bridgewater, N.J.) was mixed with a solution (30 g) of 1% CMC in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of arginine (20.1 g, 25%) and 0.30 g Crystalline DABCO. Fragrance capsule was immediately after the addition of lysine and catalyst. Formation of capsule was immediately visible by optical microscopy. The capsule slurry was transferred into a round bottom vessel and cured at 55° C. for 2 hours.

Sample 8: Polyurea Capsules Prepared With Arginine Monohydrochloride.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (120 g) containing 1.1% PVA (polyvinyl alcohol, MOWIOL 3-83; Kurray, Houston, Tex.) was combined with 30 g of DI water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of arginine monohydrochloride (20.1 g, 32%) and 0.30 g Crystalline DABCO. Formation of capsule was immediately visible by optical microscopy. The capsule slurry was transferred into a round bottom vessel and cured at 55° C. for 2 hours.

Sample 9: Polyurea Capsules Prepared With Lysine Under Basic Conditions.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% PVA (polyvinyl alcohol, MOWIOL 3-83; Kurray, Houston, Tex.) was mixed with a solution (30 g) of 1% CMC in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

A mixture containing lysine (10.1 g, 58%) and Crystalline DABCO (0.30 g) was adjusted to pH 12 by 12 mol/L sodium hydroxide. The fragrance emulsion was heated to 35° C. before the aqueous mixture was added drop-wise. Formation of capsule was immediately visible by optical microscopy. The capsule slurry was transferred into a round bottom vessel and cured at 55° C. for 2 hours.

Sample 10: Polyurea Capsules Prepared With Lysine and Sodium Carbonate Under Basic Conditions.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (130 g) containing 1.0% PVA (polyvinyl alcohol, MOWIOL 3-83; Kurray, Houston, Tex.) was mixed with a solution (30 g) of 1% CMC in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

A mixture containing lysine (10.1 g, 56%), sodium carbonate (4 g), and Crystalline DABCO (0.30 g) was adjusted to pH 12 by 12 mol/L sodium hydroxide. The fragrance emulsion was heated to 35° C. before drop-wise addition of the aqueous mixture. Formation of capsule was immediately visible by optical microscopy. The capsule slurry was transferred into a round bottom vessel and cured at 55° C. for 2 hours.

Sample 11: Polyurea Capsules Prepared With Arginine Monohydrochloride Under Basic Condition.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (120 g) containing 1.1% PVA (polyvinyl alcohol, MOWIOL 3-83; Kurray, Houston, Tex.) was mixed with a solution (30 g) of 1% CMC in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of a mixture containing arginine monohydrochloride (18.9 g, 35%), sodium hydroxide (1.2 g), and Crystalline DABCO (0.30 g). Formation of capsule was immediately visible by optical microscopy. The capsule slurry was transferred into a round bottom vessel and cured at 55° C. for 2 hours.

Sample 12: Polyurea Capsules Prepared With Arginine Monohydrochloride and Sodium Carbonate.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N100 (Bayer Corp., Pittsburgh, Pa.) to form the oil phase. In a separate beaker, a solution (120 g) containing 1.0% PVA (polyvinyl alcohol, MOWIOL 3-83; Kurray, Houston, Tex.) was mixed with a solution (30 g) of 1% CMC in DI water to form the aqueous phase. The oil phase was then emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of a mixture containing arginine monohydrochloride (16.1 g, 41%), sodium carbonate (4 g), and Crystalline DABCO (0.30 g). Formation of capsule was immediately visible by optical microscopy. The capsule slurry was transferred into a round bottom vessel and cured at 55° C. for 2 hours.

Physical Characterization of Polyurea Capsules.

Figure 2A:
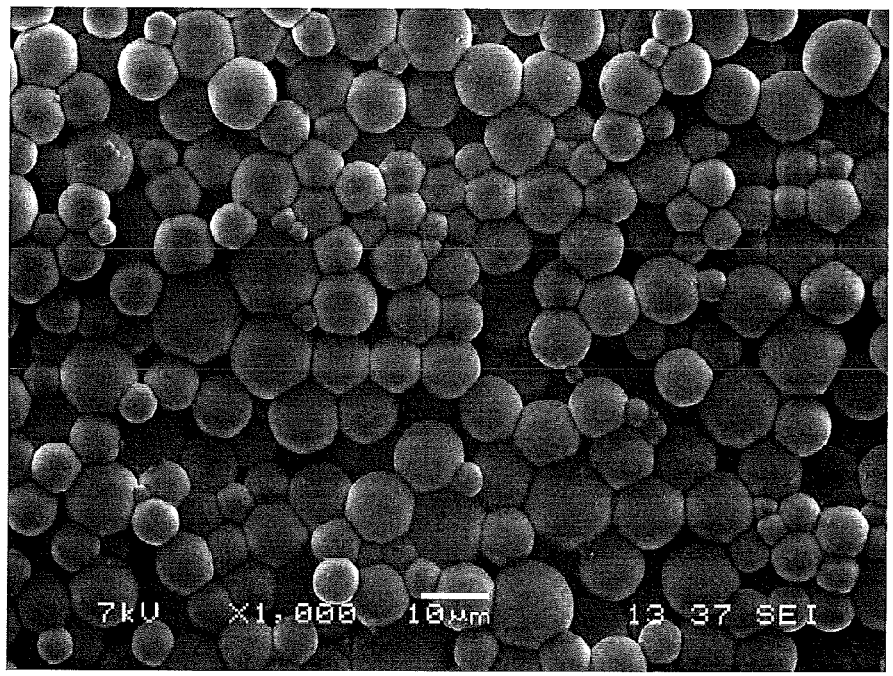
FIGS. 2A and 2B respectively show a scanning electron microscope (SEM) image and optical image of capsules from Sample 2 in Example 2.
Figure 2B:
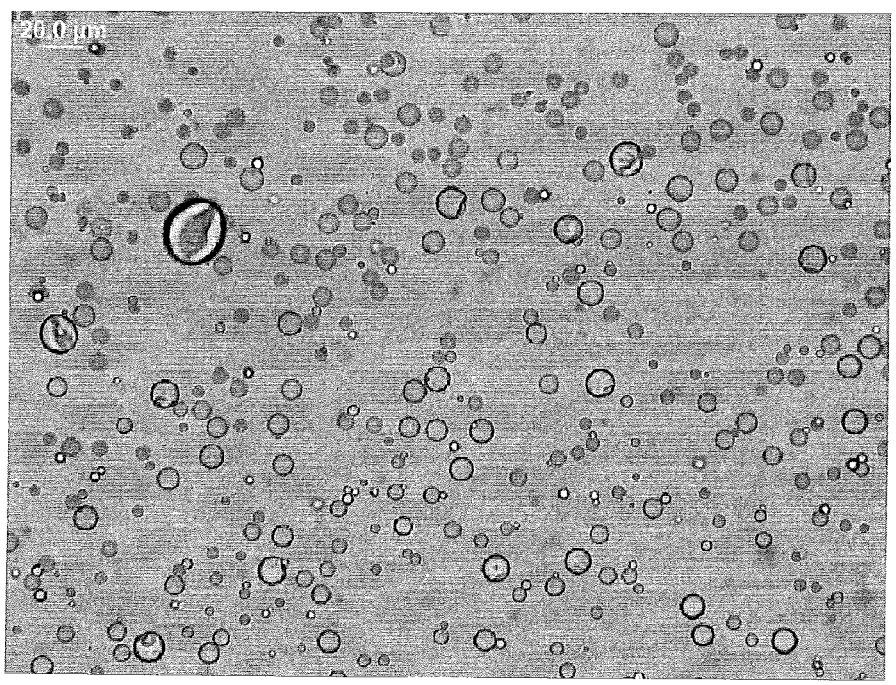

The capsules from Sample 2 were analyzed with scanning electron microscopy (FIG. 2A) and optical microscopy (FIG. 2B). It was found that the capsules prepared in accordance with the present invention have robust mechanical stability.

Encapsulation Performance of Polyurea Capsules.

The fragrance capsule slurry (Sample 2) was diluted with distilled water to yield a mixture containing 0.2% capsule slurry. One gram of the diluted capsule slurry was directly applied to each side of a 4×6 fabric swatch. Two experiments were prepared. The swatches were air-dried overnight and the headspace of the fabrics was analyzed before and after stirring with stainless steel ball bearings to rupture intact capsules. The results of this analysis are presented in Table 5.

TABLE 5

|  | Experiment 1 | | Experiment 2 | |
| --- | --- | --- | --- | --- |
|  | Unstirred | Stirred | Unstirred | Stirred |
| Headspace | 2500 | 35000 | 2600 | 55000 |
| Ratio Stirred/Unstirred | — | 14.0 | — | 21.1 |

This analysis indicated that there was a dramatic increase in headspace after the capsules were disrupted by milling. This demonstrated that increased perfumery perception can be achieved once the capsules are deposited on fabric and ruptured by physical forces.

Sensory Performance of Polyurea Capsules.

To establish the consumer benefits of the polyurea capsules, a capsule slurry prepared with an aliphatic isocyanate and amphoteric amine was blended into a roll-on base and evaluated for its consumer benefits. The fragrance load was 0.50% neat equivalent. For comparison, a similar solution was prepared using neat fragrance at 0.5%. The sample (0.3 g) was then applied to a blotter (4×6) and was allowed to dry overnight before being evaluated by a panel of 12 judges. The fragrance intensity was rated on a scale ranging from 0 to 10. A numerical value of 10 would suggest the subject generated a strong smell. The results of this analysis are presented in Table 6.

TABLE 6

| Samples | Pre-rubbing intensity | Post-rubbing intensity | $I_{post,capsule}/I_{post,neat}$ |
| --- | --- | --- | --- |
| Neat | 1.5 | 2.5 | |
| Capsule Slurry | 1.0 | 7.4 | 2.96 |

Capsules prepared with current invention had a much stronger fragrance intensity compared with neat fragrance in the post-rubbing stage and were able to deliver the full benefit of the fragrance formulation.

Example 3: Polyurea Capsules Prepared With Polyaliphatic Isocyanate and a Diamine Sample 1: Preparation of Polyurea Capsule. Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a 1.5% surfactant solution (160 g) was prepared by dissolving a sufficient amount of MORWET D-425 (Akzo Nobel, Fort Worth, Tex.) in DI water. The oil phase was emulsified into the aqueous phase under shearing (ULTRA TURRAX, T25 Basic, IKA WERKE) at 6500 rpm for two minutes to form the fragrance emulsion.

The fragrance emulsion was placed in a round bottom vessel and 10.8 g of 70% hexamethylene diamine (HMDA) (INVISTA, Wichita, Kans.) was added under constant mixing with an overhead mixer. Formation of capsule was immediately visible by optical microscopy. The mixer speed was reduced after the addition of HMDA was complete. The capsule slurry was cured at 55° C. for three hours.

Sample 2: Preparation of Polyurea Capsule With More Amine.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a 1.5% surfactant solution (160 g) was prepared by dissolving a sufficient amount of MORWET D-425 (Akzo Nobel, Fort Worth, Tex.) in DI water. The oil phase was emulsified into the aqueous phase under shearing (ULTRA TURRAX, T25 Basic, IKA WERKE) at 6500 rpm for two minutes to form the fragrance emulsion.

The fragrance emulsion was placed in a round bottom vessel and 21.6 g of 70% HMDA (INVISTA, Wichita, Kans.) was added under constant mixing with an overhead mixer. Formation of capsule was immediately visible by optical microscopy. The mixer speed was reduced after the addition of HMDA was complete. The capsule slurry was cured at 55° C. for three hours.

Sample 3: Polyurea Capsule With the Addition of HMDA at Elevated Temperature.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a 1.5% surfactant solution (160 g) was prepared by dissolving a sufficient amount of MORWET D-425 (Akzo Nobel, Fort Worth, Tex.) in DI water. The oil phase was emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of HMDA (10.8 g, 70%). Formation of capsule was immediately visible by optical microscopy. The capsule slurry was cured at 55° C. for two hours.

Sample 4: Polyurea Capsule With Addition of HMDA at Elevated Temperature and Curing at Elevated Temperature.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a 1.5% surfactant solution (160 g) was prepared by dissolving a sufficient amount of MORWET D-425 (Akzo Nobel, Fort Worth, Tex.) in DI water. The oil phase was emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of HMDA (10.8 g, 70%). Formation of capsule was immediately visible by optical microscopy. The capsule slurry was transferred into a round bottom vessel and the capsule slurry was cured at 55° C. for 2 hours and then at 80° C. for 2 hours.

Sample 5: Polyurea Capsules Prepared With a Blend of Dispersants.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a solution (130 g) containing 1.85% FLEXAN II (Akzo Nobel, Bridgewater, N.J.) was mixed with a solution (30 g) of 1% CMC in DI water to form the aqueous phase. The oil phase was emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of HMDA (10.8 g, 70%). Formation of capsule was immediately visible by optical microscopy. The capsule slurry was transferred into a round bottom vessel and the capsule slurry was cured at 55° C. for 2 hours.

Sample 6: Polyurea Capsules Prepared With a Catalyst.

Ninety-six grams of a fragrance, Greenfields (IFF, Union Beach, N.J.) was weighed out and combined with 24 g of NEOBEE oil (Stepan, Chicago, Ill.) and 9.6 g of isocyanate monomer, DESMODUR N3600 (Bayer corporation, Pittsburgh, Pa.) to form the oil phase. In a separate beaker, a solution (130 g) containing 1.85% FLEXAN II (Akzo Nobel, Bridgewater, N.J.) was mixed with a solution (30 g) of 1% CMC in DI water to form the aqueous phase. The oil phase was emulsified into the aqueous phase under shearing (ULTRA TURRAX, T25 Basic, IKA WERKE) at 6500 rpm for two minutes to form the fragrance emulsion.

The fragrance emulsion was heated to 35° C. before drop-wise addition of HMDA (10.8 g, 70%) and Crystalline DABCO catalyst 0.30 g. Formation of capsule was immediately visible by optical microscopy. The capsule slurry was transferred into a round bottom vessel and the capsule slurry was cured at 55° C. for 2 hours.

Physical Characterization of Polyurea Capsules.

SEM analysis of the capsules indicated that the capsules prepared with current invention had robust mechanical stability.

Encapsulation Performance of Polyurea Capsules.

A fragrance capsule slurry (Sample 5) was diluted with distilled water to yield a mixture containing 0.2% capsule slurry. One gram of the diluted capsule slurry was directly applied to each side of a 4×6 fabric swatch. Two experiments were prepared. The swatches were air-dried overnight and the headspace of the fabrics was analyzed before and after stirring with stainless steel ball bearings to rupture intact capsules. The results of this analysis are presented in Table 7.

TABLE 7

| | Experiment 1 | | Experiment 2 | |
| --- | --- | --- | --- | --- |
| | Unstirred | Stirred | Unstirred | Stirred |
| Headspace | 4608 | 34289 | 2600 | 88312 |
| Ratio Stirred/Unstirred | — | 7.44 | — | 34.0 |

This analysis indicated that there was a dramatic increase in headspace after the capsules were disrupted by milling. This demonstrated that increased perfumery perception can be achieved once the capsules are deposited on fabric and ruptured by physical forces.

Sensory Performance of Polyurea Capsules.

To establish the consumer benefits of the polyurea capsules, the capsule slurry was blended into a roll-on base and evaluated for its consumer benefits. The fragrance load was 0.50% neat equivalent. For comparison, a similar solution was prepared using neat fragrance at 0.5%. The sample (0.3 g) was then applied to a blotter (4×6) and was allowed to dry overnight before being evaluated by a panel of 12 judges. The fragrance intensity was rated on a scale ranging from 0 to 10. A numerical value of 10 would suggest the subject generated a strong smell. The results are presented in Table 8.

TABLE 8

| Samples | Pre-rubbing intensity | Post-rubbing intensity | $I_{post,capsule}/I_{post,neat}$ |
|---|---|---|---|
| Neat | 1.5 | 2.8 | |
| Capsule Slurry | 0.5 | 5.7 | 2.03 |

This analysis indicated that the capsules had a much stronger fragrance intensity compared with neat fragrance in the post-rubbing stage and were able to deliver the full benefit of the fragrance formulation.

What is claimed is:

1. A method for preparing a polyurea capsule composition comprising:
   (a) preparing an oil phase comprising an active material and a polyisocyanate in which the active material is a fragrance oil;
   (b) preparing a surfactant solution containing a capsule formation aid that is a mixture of polyvinyl alcohol and carboxymethyl cellulose;
   (c) emulsifying the oil phase into the surfactant solution to form a fragrance emulsion;
   (d) adding a cross-linking agent to the fragrance emulsion to form a capsule slurry; and
   (e) curing the capsule slurry,
wherein the active material is present at a level of 5% to 80% of the polyurea capsule composition; the polyisocyanate is present at a level of 1% to 7.5% of the polyurea capsule composition; the capsule formation aid is present at a level of 0.25% to 2% of the polyurea capsule composition; the cross-linking agent, being a guanidine salt, is present at a level of 0.25% to 3% of the polyurea capsule composition; the polyurea capsule composition contains a microcapsule having an encapsulating polymer that encapsulates the active material; and the encapsulating polymer is the polymerization product between the polyisocyanate and the cross-linking agent in the presence of the capsule formation aid.

2. The method of claim 1, wherein the polyisocyanate is an aromatic polyisocyanate or aliphatic polyisocyanate.

3. The method of claim 2, wherein the aliphatic polyisocyanate is a dimer, biuret, symmetric trimer, or asymmetric trimer of hexamethylene diisocyanate.

4. The method of claim 1, wherein the guanidine salt is 1,3-diaminoguanidine monohydrochloride, 1,1-dimethylbiguanide hydrochloride, guanidine carbonate or guanidine hydrochloride.

5. The method of claim 4, further comprising addition of sodium carbonate to the fragrance emulsion.

6. The method of claim 1, wherein the step of adding the cross-linking agent to the fragrance emulsion is at a temperature of 35° C.

7. The method of claim 1, wherein the step of adding the cross-linking agent to the fragrance emulsion is at a temperature of 22° C.

8. The method of claim 1, wherein the capsule slurry is cured at a temperature greater than 55° C., 65° C., 75° C., 85° C. or 95° C.

9. The method of claim 1, wherein the step of curing the capsule slurry is carried out in the presence of a catalyst.

10. The method of claim 1, further comprising the step of washing the cured capsule slurry with water.

11. The method of claim 10, further comprising the step of adding a salt to the cured capsule slurry before washing the capsule slurry with water.

* * * * *